United States Patent
Nash et al.

(10) Patent No.: US 7,696,215 B2
(45) Date of Patent: Apr. 13, 2010

(54) 4-OXOQUINAZOLIN-3-YL BENZAMIDE DERIVATIVES FOR THE TREATMENT OF CYTOKINE DISEASES

(75) Inventors: Ian Alun Nash, Cheshire (GB); Jonathan Erle Finlayson, Cheshire (GB); Caroline Rachel Thompson, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/817,137

(22) PCT Filed: Feb. 23, 2006

(86) PCT No.: PCT/GB2006/000618

§ 371 (c)(1),
(2), (4) Date: Jun. 6, 2008

(87) PCT Pub. No.: WO2006/090143

PCT Pub. Date: Aug. 31, 2006

(65) Prior Publication Data

US 2009/0124604 A1    May 14, 2009

(30) Foreign Application Priority Data

Feb. 26, 2005    (GB) ................................. 0504019.1

(51) Int. Cl.
*A61K 31/517*    (2006.01)

(52) U.S. Cl. .................... 514/266.3; 540/544; 544/290; 544/358; 548/245

(58) Field of Classification Search ................. 544/290
See application file for complete search history.

(56) References Cited

U.S. PATENT DOCUMENTS

| 7,008,945 | B1 | 3/2006 | Brown |
| 7,332,483 | B2 | 2/2008 | Brown |
| 2008/0146566 | A1 | 6/2008 | Nash et al. |

FOREIGN PATENT DOCUMENTS

| WO | WO 00/07991 | 2/2000 |
| WO | WO 00/20402 | 4/2000 |
| WO | WO 00/55153 | 9/2000 |
| WO | WO 2005/042502 | 5/2005 |
| WO | WO 2006/067444 | 6/2006 |
| WO | WO 2007/020411 | 2/2007 |

*Primary Examiner*—James O Wilson
*Assistant Examiner*—Brian McDowell

(57) ABSTRACT

The invention concerns a compound of the Formula (I) wherein m is 1-2 and each $R^1$ is a group such as cyano, halogeno, trifluoromethyl heterocyclyl and heterocyclyloxy; $R^2$ is trifluoromethyl or (1-6C)alkyl; $R^3$ is hydrogen or halogeno; and $R^4$ is isoxazolyl; or pharmaceutically-acceptable salts thereof; processes for their preparation, pharmaceutical compositions containing them and their use in the treatment of diseases or medical conditions mediated by cytokines.

9 Claims, No Drawings

4-OXOQUINAZOLIN-3-YL BENZAMIDE DERIVATIVES FOR THE TREATMENT OF CYTOKINE DISEASES

This invention relates to amide derivatives, or pharmaceutically-acceptable salts thereof which are useful as inhibitors of cytokine mediated disease. The invention also relates to processes for the manufacture of said amide derivatives, to pharmaceutical compositions containing said amide derivatives and to their use in therapeutic methods, for example by virtue of inhibition of cytokine mediated disease.

The amide derivatives disclosed in the present invention are inhibitors of the production of cytokines such as Tumour Necrosis Factor (hereinafter TNF), for example TNFα, and various members of the interleukin (hereinafter IL) family, for example IL-1, IL-6 and IL-8. Accordingly the amide derivatives of the invention will be useful in the treatment of diseases or medical conditions in which excessive production of cytokines occurs, for example excessive production of TNFα or IL-1. It is known that cytokines are produced by a wide variety of cells such as monocytes and macrophages and that they give rise to a variety of physiological effects which are believed to be important in disease or medical conditions such as inflammation and immunoregulation. For example, TNFα and IL-1 have been implicated in the cell signalling cascade which is believed to contribute to the pathology of disease states such as inflammatory and allergic diseases and cytokine-induced toxicity. It is also known that, in certain cellular systems, TNFα production precedes and mediates the production of other cytokines such as IL-1.

Abnormal levels of cytokines have also been implicated in, for example, the production of physiologically-active eicosanoids such as the prostaglandins and leukotrienes, the stimulation of the release of proteolytic enzymes such as collagenase, the activation of the immune system, for example by stimulation of T-helper cells, the activation of osteoclast activity leading to the resorption of calcium, the stimulation of the release of proteoglycans from, for example, cartilage, the stimulation of cell proliferation and to angiogenesis.

Cytokines are also believed to be implicated in the production and development of disease states such as inflammatory and allergic diseases, for example inflammation of the joints (especially rheumatoid arthritis, osteoarthritis and gout), inflammation of the gastrointestinal tract (especially inflammatory bowel disease, ulcerative colitis, Crohn's disease and gastritis), skin disease (especially psoriasis, eczema and dermatitis) and respiratory disease (especially asthma, bronchitis, allergic rhinitis, chronic obstructive pulmonary disease and adult respiratory distress syndrome), and in the production and development of various cardiovascular and cerebrovascular disorders such as congestive heart failure, acute heart failure, myocardial infarction, the formation of atherosclerotic plaques, hypertension, platelet aggregation, angina, stroke, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoperosis and periodontitis, and the abnormal changes in bone metabolism which may accompany rheumatoid arthritis and osteoarthritis. Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke. Excessive cytokine production has also been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), chronic obstructive pulmonary disease, tumour invasiveness and tumour metastasis and multiple sclerosis. Excessive cytokine production has also been implicated in pain.

Evidence of the central role played by TNFα in the cell signalling cascade which gives rise to rheumatoid arthritis is provided by the efficacy in clinical studies of antibodies of TNFα (*The Lancet*, 1994, 344, 1125 and *British Journal of Rheumatology*, 1995, 34, 334).

Thus cytokines such as TNFα and IL-1 are believed to be important mediators of a considerable range of diseases and medical conditions. Accordingly it is expected that inhibition of the production of and/or effects of these cytokines will be of benefit in the prophylaxis, control or treatment of such diseases and medical conditions.

Without wishing to imply that the amide derivatives disclosed in the present invention possesses pharmacological activity only by virtue of an effect on a single biological process, it is believed that the amide derivatives inhibit the effects of cytokines by virtue of inhibition of the enzyme p38 kinase. p38 kinase, otherwise known as cytokine suppressive binding protein (hereinafter CSBP) and reactivating kinase (hereinafter RK), is a member of the mitogen-activated protein (hereinafter MAP) kinase family of enzymes which is known to be activated by physiological stress such as that induced by ionising radiation, cytotoxic agents, and toxins, for example endotoxins such as bacterial lipopolysaccharide, and by a variety of agents such as the cytokines, for example TNFα, and IL-1. It is known that p38 kinase phosphorylates certain intracellular proteins which are involved in the cascade of enzymatic steps which leads to the biosynthesis and excretion of cytokines such as TNFα and IL-1. Known inhibitors of p38 kinase have been reviewed by G. J. Hanson in *Expert Opinions on Therapeutic Patents*, 1997, 7, 729-733. p38 kinase is known to exist in isoforms identified as p38α and p38β.

The amide derivatives disclosed in the present invention are inhibitors of the production of cytokines such as TNF, in particular of TNFα, and various interleukins, in particular IL-1.

It is known from the International Patent Application WO 00/55153, that certain benzamide derivatives are inhibitors of the production of cytokines such as TNF, and various interleukins. One of the disclosed compounds is 3-[5-(2-chloropyrid-4-ylcarbonylamino)-2-methylphenyl]-6-(4-methylpiperazin-1-yl)-3,4-dihydroquinazolin-4-one.

There is no disclosure in this document of an amide derivative which bears isoxazolylaminocarbonyl substituent at the 3-position of the central 6-methylphenyl core. We have now found that such compounds possess potent cytokine inhibitory activity and have desirable pharmacological activity profiles. There is a need for such compounds.

According to the first aspect of present invention there is provided a compound of the Formula I

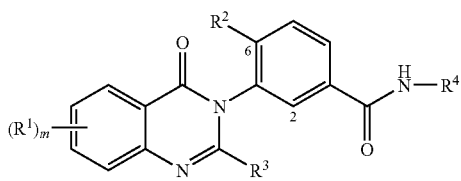

wherein m is 0, 1 or 2;

R¹ is halogeno, hydroxy, cyano, trifluoromethyl, trifluoromethoxy, (1-6C)alkyl, (1-6C)alkoxy, (2-6C)alkenyl, (2-6C)alkynyl, (2-6C)alkanoyl, (1-6C)alkylthio, (1-6C)alkylsulphinyl, (1-6C)alkylsulphonyl, hydroxy-(2-6C)alkoxy, amino-(2-6C)alkoxy, cyano-(2-6C)alkoxy, (1-6C)alkylamino-(2-6C)alkoxy, di-[(1-6C)alkyl]amino-(2-6C)alkoxy, (1-6C)alkoxy-(2-6C)alkoxy, carbamoyl-(1-6C)alkoxy, N-(1-6C)alkylcarbamoyl-(1-6C)alkoxy, amino-(1-6C)alkyl, (1-6C)alkylamino-(1-6C)alkyl, di[(1-6C)alkyl]amino-(1-6C)alkyl, carbamoyl-(1-6C)alkyl, N-(1-6C)alkylcarbamoyl-(1-6C)alkyl, hydroxy-(2-6C)alkylamino, cyano-(2-6C)alkylamino, halogeno-(2-6C)alkylamino, amino-(2-6C)alkylamino, (1-6C)alkoxy-(2-6C)alkylamino, (1-6C)alkylamino-(2-6C)alkylamino, di-[(1-6C)alkyl]amino-(2-6C)alkylamino, heteroaryl, heteroaryl-(1-6C)alkyl, heteroaryloxy, heteroaryl-(1-6C)alkoxy, heteroarylamino, heterocyclyl, heterocyclyl-(1-6C)alkyl, heterocyclyloxy, heterocyclyl-(1-6C)alkoxy and heterocyclylamino, and wherein any aryl, heteroaryl or heterocyclyl group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the R¹ substituents defined hereinbefore which comprises a CH₂ group which is attached to 2 carbon atoms or a CH₃ group which is attached to a carbon or nitrogen atom may optionally bear on each said CH₂ or CH₃ group one or more substituents selected from halogeno, hydroxy, amino, trifluoromethyl, trifluoromethoxy, oxo, carboxy, carbamoyl, acetamido, (1-6C)alkyl, (2-6C)alkenyl, (2-6C)alkynyl, (3-6C)cycloalkyl, (3-6C)cycloalkoxy, (1-6C)alkoxy, (1-6C)alkylamino, di-[(1-6C)alkyl]amino, hydroxy-(1-6C)alkyl, (1-6C)alkoxy-(1-6C)alkyl, halogeno-(1-6C)alkyl, (1-6C)alkoxy-(2-6C)alkoxy, (1-6C)alkoxycarbonyl, carbamoyl, N-(1-6C)alkylcarbamoyl, N,N-di-[(1-6C)alkyl]carbamoyl, (1-6C)sulphonyl, (1-6C)sulphamoyl, heteroaryl, heteroaryl-(1-6C)alkyl, heterocyclyl and heterocyclyloxy, and wherein any heterocyclyl group in a R¹ substituent may optionally bear 1 or 2 oxo or thioxo substituents;

R² is halogeno, trifluoromethyl or (1-6C)alkyl;

R³ is hydrogen, halogeno or (1-6C)alkyl; and

R⁴ is isoxazolyl, and R⁴ may be optionally substituted by one or more substituents selected from halogeno, hydroxy, amino, (1-6C)alkyl, (2-6C)alkenyl, (2-6C)alkynyl, (1-6C)alkoxy, (1-6C)alkylamino and di-[(1-6C)alkyl]amino;

or a pharmaceutically-acceptable salt thereof.

In this specification, the term (1-6C)alkyl includes straight-chain and branched-chain alkyl groups such as propyl, isopropyl and tert-butyl. References to individual alkyl groups such as "propyl" are specific for the straight-chain version only, references to individual branched-chain alkyl groups such as "isopropyl" are specific for the branched-chain version only. In this specification, the term (3-6C)cycloalkyl includes cyclopropyl, cyclobutyl, cyclopentyl, cyclopentenyl, and cyclohexyl. References to individual cycloalkyl groups such as "cyclopentyl" are specific for that 5-membered ring only.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting cytokines, in particular TNF. The synthesis of optically active forms may be carried out by standard techniques of organic chemistry well known in the art, for example by synthesis from optically active starting materials or by resolution of a racemic form. Similarly, inhibitory properties against TNF may be evaluated using the standard laboratory techniques referred to hereinafter.

Suitable values for the generic radicals referred to above include those set out below.

A suitable value for R¹ when it is aryl is, for example, phenyl, indenyl, indanyl, naphthyl, tetrahydronaphthyl or fluorenyl, preferably phenyl.

A suitable value for R¹ when it is heteroaryl is, for example, an aromatic 5- or 6-membered monocyclic ring, a 9- or 10-membered bicyclic ring or a 13- or 14-membered tricyclic ring each with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl, naphthyridinyl, carbazolyl, dibenzofuranyl, dibenzothiophenyl, S,S-dioxodibenzothiophenyl, xanthenyl, dibenzo-1,4-dioxinyl, phenoxathiinyl, phenoxazinyl, dibenzothiinyl, phenothiazinyl, thianthrenyl, benzofuropyridyl, pyridoindolyl, acridinyl or phenanthridinyl, preferably furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl, more preferably furyl, thienyl, isoxazolyl, thiazolyl, pyridyl, benzothienyl, benzofurazanyl, quinolyl, carbazolyl, dibenzofuranyl or dibenzothiophenyl.

A suitable value for R¹ when it is heterocyclyl is, for example, a non-aromatic saturated or partially saturated 3- to 10-membered monocyclic or bicyclic ring or a 5- to 7-membered monocyclic ring each with up to five heteroatoms selected from oxygen, nitrogen and sulphur, for example oxiranyl, oxetanyl, azetidinyl, tetrahydrofuranyl, tetrahydropyranyl, pyrrolinyl, pyrrolidinyl, imidazolinyl, imidazolidinyl, pyrazolinyl, pyrazolidinyl, 1,1-dioxidoisothiazolidinyl, morpholinyl, thiomorpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl or benzo derivatives thereof such as 2,3-dihydrobenzofuranyl, 2,3-dihydrobenzothienyl, indolinyl, isoindolinyl, chromanyl and isochromanyl, preferably azetidin-1-yl, 3-pyrrolin-1-yl, pyrrolidin-1-yl, pyrrolidin-2-yl, 1,1-dioxidoisothiazolidin-2-yl, morpholino, 1,1-dioxotetrahydro-4H-1,4-thiazin-4-yl, piperidin-3-yl, piperidin-4-yl, homopiperidin-1-yl, piperidino, piperazin-1-yl or homopiperazin-1-yl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for a substituent within $R^1$ when it is (3-6C)cycloalkyl is, for example, a saturated monocyclic 3- to 6-membered carbon ring such as cyclopropyl, cyclobutyl, cyclopentyl or cyclohexyl, preferably cyclopropyl, cyclopentyl or cyclobutyl, more preferably cyclopropyl.

A suitable value for a substituent within $R^1$ when it is (3-6C)cycloalkyl-(1-6C)alkyl is, for example, cyclopropylmethyl, cyclobutylmethyl, cyclopentylmethyl, cyclohexylmethyl, cyclopropylethyl, preferably cyclopropylmethyl or cyclopropylethyl, more preferably cyclopropylmethyl.

Suitable values for various $R^1$, $R^2$ or $R^3$ groups, or for various substituents on $R^1$ or $R^4$ or on an aryl, heteroaryl or heterocyclyl group within $R^1$ include:— for halogeno: fluoro, chloro, bromo and iodo;
for (1-6C)alkyl: methyl, ethyl, propyl, isopropyl and tert-butyl;
for (2-6C)alkenyl: vinyl and allyl;
for (2-6C)alkynyl: ethynyl and 2-propynyl;
for (1-6C)alkoxy: methoxy, ethoxy, propoxy, isopropoxy and butoxy;
for (1-6C)alkylthio: methylthio, ethylthio and propylthio;
for (1-6C)alkylsulphinyl: methylsulphinyl, ethylsulphinyl and propylsulphinyl;
for (1-6C)alkylsulphonyl: methylsulphonyl, ethylsulphonyl and propylsulphonyl;
for hydroxy-(2-6C)alkoxy: 2-hydroxyethoxy, 3-hydroxypropoxy, 2-hydroxy-1-methylethoxy, 2-hydroxy-2-propoxy and 4-hydroxybutoxy;
for cyano-(1-6C)alkoxy: cyanomethoxy, 2-cyanoethoxy and 3-cyanopropoxy;
for (1-6C)alkoxy-(2-6C)alkoxy: 2-methoxyethoxy, 2-ethoxyethoxy, 3-methoxypropoxy, 2-methoxy-1-methylethoxy and 4-ethoxybutoxy;
for carbamoyl-(1-6C)alkoxy: carbamoylmethoxy and 2-carbamoylethoxy;
for N-(1-6C)alkylcarbamoyl-(1-6C)alkoxy: N-methylcarbamoylmethoxy, 2-(N-ethylcarbamoyl)ethoxy and 3-(N-methylcarbamoyl)propoxy;
for (3-6C)cycloalkyl-(1-6C)alkyl (3-6C)cycloalkylmethyl and (3-6C)cycloalkylethyl;
for (1-6C)alkylamino: methylamino, ethylamino and propylamino;
for di-[(1-6C)alkyl]amino: dimethylamino, diethylamino and N-ethyl-N-methylamino;
for (1-6C)alkoxycarbonyl: methoxycarbonyl, ethoxycarbonyl, propoxycarbonyl and tert-butoxycarbonyl;
for N-(1-6C)alkylcarbamoyl: N-methylcarbamoyl, N-ethylcarbamoyl and N-propylcarbamoyl;
for N,N-di-[(1-6C)alkyl]carbamoyl: N,N-dimethylcarbamoyl, N-ethyl-N-methylcarbamoyl and N,N-diethylcarbamoyl;
for (2-6C)alkanoyl: acetyl and propionyl;

for halogeno-(1-6C)alkyl: fluoromethyl, chloromethyl, bromomethyl, difluoromethyl, dichloromethyl, dibromomethyl, 2-fluoroethyl, 2-chloroethyl and 2-bromoethyl;
for hydroxy-(1-6C)alkyl: hydroxymethyl, 2-hydroxyethyl, 1-hydroxyethyl and 3-hydroxypropyl;
for carbamoyl-(1-6C)alkyl: carbamoylmethyl, 1-carbamoylethyl, 2-carbamoylethyl and 3-carbamoylpropyl;
for N-(1-6C)alkylcarbamoyl-(1-6C)alkyl: N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;
for (1-6C)alkoxy-(1-6C)alkyl: methoxymethyl, ethoxymethyl, 1-methoxyethyl, 2-methoxyethyl, 2-ethoxyethyl and 3-methoxypropyl;
for amino-(1-6C)alkyl: aminomethyl, 2-aminoethyl, 1-aminoethyl and 3-aminopropyl;
for carboxy-(1-6C)alkyl: carboxymethyl, 1-carboxyethyl, 2-carboxyethyl, 3-carboxypropyl and 4-carboxybutyl;
for cyano-(1-6C)alkyl: cyanomethyl, 2-cyanoethyl, 1-cyanoethyl and 3-cyanopropyl;
for (1-6C)alkylamino-(1-6C)alkyl: methylaminomethyl, ethylaminomethyl, 1-methylaminoethyl, 2-methylaminoethyl, 2-ethylaminoethyl and 3-methylaminopropyl;
for di-[(1-6C)alkyl]amino-(1-6C)alkyl: dimethylaminomethyl, diethylaminomethyl, 1-dimethylaminoethyl, 2-dimethylaminoethyl and 3-dimethylaminopropyl.
for amino-(2-6C)alkoxy: 2-aminoethoxy, 2-amino-1-methylethoxy, 3-aminopropoxy, 2-amino-2-methylpropoxy and 4-aminobutoxy;
for (1-6C)alkylamino-(2-6C)alkoxy: 2-methylaminoethoxy, 2-methylamino-1-methylethoxy, and 3-ethylaminopropoxy,
for di-[(1-6C)alkyl]amino-(2-6C)alkoxy: 2-dimethylaminoethoxy, 2-diethylaminoethoxy, 2-dimethylaminopropoxy, 2-dimethylamino-2-methylethoxy, 3-dimethylaminopropoxy and 4-dimethylaminobutoxy, 2-(N-methyl-N-isopropylamino)ethoxy, and 2-(N-ethyl-N-isopropylamino)ethoxy;
for amino-(2-6C)alkylamino: 2-aminoethylamino, 3-aminopropylamino, 2-amino-2-methylpropylamino and 4-aminobutylamino;
for halogeno-(2-6C)alkylamino: 2-fluoroethylamino, 2-chloroethylamino, 2-bromoethylamino, 3-fluoropropylamino and 3-chloropropylamino;
for hydroxy-(2-6C)alkylamino: 2-hydroxyethylamino, 3-hydroxypropylamino, 2-hydroxy-2-methylpropylamino and 4-hydroxybutylamino;
for cyano-(1-6C)alkylamino: cyanomethylamino, 2-cyanoethylamino and 3-cyanopropylamino;
for (1-6C)alkoxy-(2-6C)alkylamino: 2-methoxyethylamino, 2-ethoxyethylamino, 3-methoxypropylamino and 3-ethoxypropylamino;
for (1-6C)alkylamino-(2-6C)alkylamino: 2-methylaminoethylamino, 2-ethylaminoethylamino, 2-propylaminoethylamino, 3-methylaminopropylamino, 3-ethylaminopropylamino, 2-methylamino-2-methylpropylamino and 4-methylaminobutylamino;
for di-[(1-6C)alkyl]amino-(2-6C)alkylamino: 2-dimethylaminoethylamino, 2-(N-ethyl-N-methylamino)ethylamino, 2-diethylaminoethylamino, 2-dipropylaminoethylamino, 3-dimethylaminopropylamino, 3-diethylaminopropylamino, 2-dimethylamino-2-methylpropylamino and 4-dimethylaminobutylamino;

Suitable values for $R^1$ and suitable values for a substituent on $R^1$ or $R^4$ include:— for aryl-(1-6C)alkyl: benzyl, 2-phenylethyl, 2-phenylpropyl and 3-phenylpropyl;

for aryl-(1-6C)alkoxy: benzyloxy and 2-phenylethoxy;

for aryloxy: phenoxy and 2-naphthyloxy;

for arylamino: anilino;

for heteroaryl-(1-6C)alkyl: heteroarylmethyl, heteroarylethyl, 2-heteroarylethyl, 2-heteroarylpropyl and 3-heteroarylpropyl;

for heteroaryl-(1-6C)alkoxy: heteroarylmethoxy and 2-heteroarylethoxy;

for heterocyclyl-(1-6C)alkyl: heterocyclylmethyl, 2-heterocyclylethyl, 2-heterocyclylpropyl and 3-heterocyclylpropyl;

for heterocyclyl-(1-6C)alkoxy: heterocyclylmethoxy and 2-heterocyclylethoxy;

for (2-6C)alkanoyloxy: acetoxy and propionyloxy:

for (1-6C)alkanoylamino: formamido, acetamido and propionamido;

for (1-6C)alkoxycarbonyl-(1-6C)alkyl: methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;

A suitable pharmaceutically-acceptable salt of a compound of the Formula I, for example, an acid-addition salt of a compound of the Formula I which is sufficiently basic, for example, an acid-addition salt with an inorganic or organic acid such as hydrochloric, hydrobromic, sulphuric, phosphoric, trifluoroacetic, citric, maleic, tartaric, fumaric, hemifumaric, succinic, hemisuccinic, mandelic, methanesulphonic, dimethanesulphonic, ethane-1,2-sulphonic, benzenesulphonic, salicylic or 4-toluenesulphonic acid.

Further values of m, $R^1$, $R^2$, $R^3$ and $R^4$ are as follows. Such values may be used where appropriate with any of the definitions, claims or embodiments defined hereinbefore or hereinafter.

m is 0, 1 or 2.

m is 1 or 2.

m is 1.

m is 2.

$R^1$ is halogeno, hydroxy, cyano, trifluoromethyl, trifluoromethoxy, (1-6C)alkyl, (1-6C)alkoxy, (2-6C)alkenyl, (2-6C)alkynyl, (2-6C)alkanoyl, (1-6C)alkylthio, (1-6C)alkylsulphonyl, hydroxy-(2-6C)alkoxy, amino-(2-6C)alkoxy, cyano-(2-6C)alkoxy, (1-6C)alkylamino-(2-6C)alkoxy, di-[(1-6C)alkyl]amino-(2-6C)alkoxy, (1-6C)alkoxy-(2-6C)alkoxy, di[(1-6C)alkyl]amino-(1-6C)alkyl, carbamoyl-(1-6C)alkyl, heteroaryl-(1-6C)alkyl, heteroaryl-(1-6C)alkoxy, heterocyclyl, heterocyclyl-(1-6C)alkyl, heterocyclyloxy and heterocyclyl-(1-6C)alkoxy, and wherein any heteroaryl or heterocyclyl group in a $R^1$ substituent may optionally bear 1 or 2 substituents selected from hydroxy, halogeno, (1-6C)alkyl, (3-6C)cycloalkyl-(1-6C)alkyl, (3-6C)cycloalkyl-(1-6C)alkoxy, (1-6C)alkoxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, and wherein any of the $R^1$ substituents defined hereinbefore which comprises a $CH_2$ group which is attached to 2 carbon atoms or a $CH_3$ group which is attached to a carbon or nitrogen atom may optionally bear on each said $CH_2$ or $CH_3$ group one or more substituents selected from halogeno, hydroxy, trifluoromethyl, oxo(1-6C)alkyl, (2-6C)alkenyl, (2-6C)alkynyl, (3-6C)cycloalkyl, (1-6C)alkoxy, (1-6C)alkylamino, di-[(1-6C)alkyl]amino, hydroxy-(1-6C)alkyl, (1-6C)alkoxy-(1-6C)alkyl, halogeno-(1-6C)alkyl, (1-6C)alkoxycarbonyl, heteroaryl, heteroaryl-(1-6C)alkyl, heterocyclyl and heterocyclyloxy, and wherein any heterocyclyl group in a $R^1$ substituent may optionally bear 1 or 2 oxo or thioxo substituents.

$R^1$ is halogeno, hydroxy, (1-6C)alkoxy, (2-6C)alkenyl, (2-6C)alkynyl, (2-6C)alkanoyl, (1-6C)alkylthio, (1-6C)alkylsulphonyl, amino-(2-6C)alkoxy, (1-6C)alkylamino-(2-6C)alkoxy, di-[(1-6C)alkyl]amino-(2-6C)alkoxy, di[(1-6C)alkyl]amino-(1-6C)alkyl, carbamoyl-(1-6C)alkyl, heteroaryl-(1-6C)alkyl, heterocyclyl, heterocyclyloxy and heterocyclyl-(1-6C)alkoxy, and wherein any heteroaryl or heterocyclyl group in a $R^1$ substituent may optionally bear 1 or 2 substituents selected from hydroxy, halogeno, (1-6C)alkyl, (3-6C)cycloalkyl-(1-6C)alkyl, (3-6C)cycloalkyl-(1-6C)alkoxy, (1-6C)alkoxy, (1-6C)alkoxycarbonyl-(1-6C)alkyl, N-(1-6C)alkylcarbamoyl, N,N-di-[(1-6C)alkyl]carbamoyl, halogeno-(1-6C)alkyl, hydroxy-(1-6C)alkyl, (1-6C)alkoxy-(1-6C)alkyl, cyano-(1-6C)alkyl, and wherein any of the $R^1$ substituents defined hereinbefore which comprises a $CH_2$ group which is attached to 2 carbon atoms or a $CH_3$ group which is attached to a carbon or nitrogen atom may optionally bear on each said $CH_2$ or $CH_3$ group one or more substituents selected from halogeno, hydroxy, trifluoromethyl, (1-6C)alkyl, (3-6C)cycloalkyl, (1-6C)alkoxy, di-[(1-6C)alkyl]amino, (1-6C)alkoxy-(1-6C)alkyl, (1-6C)alkoxycarbonyl, heteroaryl-(1-6C)alkyl, heterocyclyl and heterocyclyloxy.

$R^1$ is halogeno, hydroxy, (1-6C)alkoxy, (2-6C)alkenyl, (2-6C)alkynyl, (2-6C)alkanoyl, (1-6C)alkylthio, (1-6C)alkylsulphonyl, amino-(2-6C)alkoxy, (1-6C)alkylamino-(2-6C)alkoxy, di-[(1-6C)alkyl]amino-(2-6C)alkoxy, di[(1-6C)alkyl]amino-(1-6C)alkyl, carbamoyl-(1-6C)alkyl, heteroaryl-(1-6C)alkyl, heterocyclyl, heterocyclyloxy and heterocyclyl-(1-6C)alkoxy, and wherein any heteroaryl or heterocyclyl group in a $R^1$ substituent may optionally bear 1 or 2 substituents selected from hydroxy, halogeno, (1-6C)alkyl, (3-6C)cycloalkyl-(1-6C)alkyl, (3-6C)cycloalkyl-(1-6C)alkoxy, (1-6C)alkoxy, (1-6C)alkoxycarbonyl-(1-6C)alkyl, N-(1-6C)alkylcarbamoyl, N,N-di-[(1-6C)alkyl]carbamoyl, halogeno-(1-6C)alkyl, hydroxy-(1-6C)alkyl, (1-6C)alkoxy-(1-6C)alkyl, cyano-(1-6C)alkyl, and wherein any of the $R^1$ substituents defined hereinbefore which comprises a $CH_2$ group which is attached to 2 carbon atoms or a $CH_3$ group which is attached to a carbon or nitrogen atom may optionally bear on each said $CH_2$ or $CH_3$ group one or more substituents selected from halogeno, hydroxy, trifluoromethyl, (1-6C)alkyl, (3-6C)cycloalkyl, (1-6C)alkoxy, di-[(1-6C)alkyl]amino, (1-6C)alkoxy-(1-6C)alkyl, (1-6C)alkoxycarbonyl, heteroaryl-(1-6C)alkyl, heterocyclyl and heterocyclyloxy.

$R^1$ is fluoro, chloro, bromo, iodo, hydroxy, methoxy, ethoxy, propoxy, acetyl, methylthio, ethylthio, methylsulphonyl, ethylsulphonyl, 2-aminoethoxy, 2-amino-1-methylethoxy, 3-aminopropoxy, 2-amino-2-methylpropoxy, 2-methylaminoethoxy, 2-methylamino-1-methylethoxy, 3-ethylaminopropoxy, 2-dimethylaminoethoxy, 2-diethylaminoethoxy, 2-dimethylaminopropoxy, 2-dimethylamino-2-methylethoxy, 3-dimethylaminopropoxy, dimethylaminomethyl, diethylaminomethyl, 1-dimethylaminoethyl, 2-dimethylaminoethyl, 3-dimethylaminopropyl, carbamoylmethyl, 1-carbamoylethyl, 2-carbamoylethyl, 3-carbamoylpropyl, heteroarylmethyl, heteroarylethyl, heterocyclyl, heterocyclyloxy, heterocyclylmethoxy and 2-heterocyclylethoxy, and wherein any heteroaryl or heterocyclyl group in a R¹ substituent may optionally bear 1 or 2 substituents selected from hydroxy, is fluoro, chloro, bromo, iodo, methyl, ethyl, propyl, isopropyl, cyclobutylmethyl, cyclopropylmethyl, cyclobutylmethoxy, cyclopropylmethoxy, acetyl, methoxy, ethoxy, propoxy, methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl, 3-ethoxycarbonylpropyl, N-methylcarbamoyl, N-ethylcarbamoyl, N-propylcarbamoyl, N,N-dimethylcarbamoyl, N-ethyl-N-methylcarbamoyl, N,N-diethylcarbamoyl, fluoromethyl, chloromethyl, bromomethyl, difluoromethyl, dichloromethyl, dibromomethyl, 2-fluoroethyl, 2-chloroethyl, 2-bromoethyl, hydroxymethyl, 2-hydroxyethyl, 1-hydroxyethyl, 3-hydroxypropyl, methoxymethyl, ethoxymethyl, 1-methoxyethyl, 2-methoxyethyl, 2-ethoxyethyl and 3-methoxypropyl, cyanomethyl, 2-cyanoethyl, 1-cyanoethyl, 3-cyanopropyl, and wherein any of the R¹ substituents defined hereinbefore which comprises a CH₂ group which is attached to 2 carbon atoms or a CH₃ group which is attached to a carbon or nitrogen atom may optionally bear on each said CH₂ or CH₃ group one or more substituents selected from fluoro, chloro, bromo, iodo, hydroxy, trifluoromethyl, methyl, ethyl, propyl, isopropyl, tert-butyl, cyclopropyl, cyclobutyl, cyclopentyl, methoxy, ethoxy, propoxy, isopropoxy, tert-butoxy, dimethylamino, diethylamino, N-ethyl-N-methylamino, methoxymethyl, ethoxymethyl, 1-methoxyethyl, 2-methoxyethyl, 2-ethoxyethyl, 3-methoxypropyl, methoxycarbonyl, ethoxycarbonyl, propoxycarbonyl, tert-butoxycarbonyl, heteroarylmethyl, heteroarylethyl, heterocyclyl and heterocyclyloxy.

R¹ is fluoro, chloro, bromo, iodo, hydroxy, methoxy, ethoxy, propoxy, acetyl, methylthio, ethylthio, methylsulphonyl, ethylsulphonyl, 2-aminoethoxy, 2-amino-1-methylethoxy, 3-aminopropoxy, 2-amino-2-methylpropoxy, 2-methylaminoethoxy, 2-methylamino-1-methylethoxy, 3-ethylaminopropoxy, 2-dimethylaminoethoxy, 2-diethylaminoethoxy, 2-dimethylaminopropoxy, 2-dimethylamino-2-methylethoxy, 3-dimethylaminopropoxy, dimethylaminomethyl, diethylaminomethyl, 1-dimethylaminoethyl, 2-dimethylaminoethyl, 3-dimethylaminopropyl, carbamoylmethyl, 1-carbamoylethyl, 2-carbamoylethyl, 3-carbamoylpropyl, piperidinylmethyl, piperidinylethyl, homopiperidinyl, piperazinyl, homopiperazinyl, morpholinyl, dihydropyridinyl, tetrahydropyridinyl, dihydropyrimidinyl or tetrahydropyrimidinyl, piperidinyloxy, pyrrolidinyloxy, morpholinylethoxy, pyrrolidinylethoxy, piperidinylethoxy, azetidinylethoxy, and wherein any heteroaryl or heterocyclyl group in a R¹ substituent may optionally bear 1 or 2 substituents selected from hydroxy, is fluoro, chloro, bromo, iodo, methyl, ethyl, propyl, isopropyl, cyclobutylmethyl, cyclopropylmethyl, cyclobutylmethoxy, cyclopropylmethoxy, acetyl, methoxy, ethoxy, propoxy, methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl, 3-ethoxycarbonylpropyl, N-methylcarbamoyl, N-ethylcarbamoyl, N-propylcarbamoyl, N,N-dimethylcarbamoyl, N-ethyl-N-methylcarbamoyl, N,N-diethylcarbamoyl, fluoromethyl, chloromethyl, bromomethyl, difluoromethyl, dichloromethyl, dibromomethyl, 2-fluoroethyl, 2-chloroethyl, 2-bromoethyl, hydroxymethyl, 2-hydroxyethyl, 1-hydroxyethyl, 3-hydroxypropyl, methoxymethyl, ethoxymethyl, 1-methoxyethyl, 2-methoxyethyl, 2-ethoxyethyl and 3-methoxypropyl, cyanomethyl, 2-cyanoethyl, 1-cyanoethyl, 3-cyanopropyl, and wherein any of the R¹ substituents defined hereinbefore which comprises a CH₂ group which is attached to 2 carbon atoms or a CH₃ group which is attached to a carbon or nitrogen atom may optionally bear on each said CH₂ or CH₃ group one or more substituents selected from fluoro, chloro, bromo, iodo, hydroxy, trifluoromethyl, methyl, ethyl, propyl, isopropyl, tert-butyl, cyclopropyl, cyclobutyl, cyclopentyl, methoxy, ethoxy, propoxy, isopropoxy, tert-butoxy, dimethylamino, diethylamino, N-ethyl-N-methylamino, methoxymethyl, ethoxymethyl, 1-methoxyethyl, 2-methoxyethyl, 2-ethoxyethyl, 3-methoxypropyl, methoxycarbonyl, ethoxycarbonyl, propoxycarbonyl, tert-butoxycarbonyl, piperidinylmethyl, piperidinylethyl, homopiperidinyl, piperazinyl, homopiperazinyl, morpholinyl, dihydropyridinyl, tetrahydropyridinyl, dihydropyrimidinyl, tetrahydropyrimidinyl, piperidinyloxy and pyrrolodinyloxy.

R¹ is amino-(2-6C)alkoxy, (1-6C)alkylamino-(2-6C)alkoxy, di-[(1-6C)alkyl]amino-(2-6C)alkoxy, amino-(2-6C)alkylamino, (1-6C)alkylamino-(2-6C)alkylamino, di-[(1-6C)alkyl]amino-(2-6C)alkylamino, aryl, aryl-(1-6C)alkyl, aryl-(1-6C)alkoxy, aryloxy, arylamino, heteroaryl, heteroaryl-(1-6C)alkyl, heteroaryloxy, heteroaryl-(1-6C)alkoxy, heteroarylamino, heterocyclyl, heterocyclyl-(1-6C)alkyl, heterocyclyloxy, heterocyclyl-(1-6C)alkoxy or heterocyclylamino, and wherein any aryl, heteroaryl or heterocyclyl group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the R¹ substituents defined hereinbefore which comprises a CH₂ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino, and wherein any heterocyclyl group in a R¹ substituent may optionally bear 1 or 2 oxo or thioxo substituents.

R¹ is aryl, aryl-(1-6C)alkyl, aryl-(1-6C)alkoxy, aryloxy, arylamino, heteroaryl, heteroaryl-(1-6C)alkyl, heteroaryloxy, heteroaryl-(1-6C)alkoxy, heteroarylamino, heterocyclyl, heterocyclyl-(1-6C)alkyl, heterocyclyloxy, heterocyclyl-(1-6C)alkoxy or heterocyclylamino, and wherein any aryl, heteroaryl or heterocyclyl group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)

alkoxy-(1-6C)alkyl, cyano-(1-6C)alkyl, carboxy-(1-6C) alkyl, amino-(1-6C)alkyl, (1-6C)alkylamino-(1-6C)alkyl and di-[(1-6C)alkyl]amino-(1-6C)alkyl, and wherein any of the R¹ substituents defined hereinbefore which comprises a CH₂ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino, and wherein any heterocyclyl group in a R¹ substituent may optionally bear 1 or 2 oxo or thioxo substituents.

R¹ is amino-(2-6C)alkoxy, (1-6C)alkylamino-(2-6C)alkoxy, di-[(1-6C)alkyl]amino-(2-6C)alkoxy, amino-(2-6C)alkylamino, (1-6C)alkylamino-(2-6C)alkylamino or di-[(1-6C)alkyl]amino-(2-6C)alkylamino, and wherein any of the R¹ substituents defined hereinbefore which comprises a CH₂ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino.

R¹ is heterocyclyl, heterocyclyl-(1-6C)alkyl, heterocyclyloxy, heterocyclyl-(1-6C)alkoxy or heterocyclylamino, and wherein any heterocyclyl group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the R¹ substituents defined hereinbefore which comprises a CH₂ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino.

R¹ is heterocyclyl, heterocyclyloxy or heterocyclyl-(1-6C)alkoxy, and wherein any heterocyclyl group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the R¹ substituents defined hereinbefore which comprises a CH₂ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino.

R¹ is heterocyclyl or heterocyclyloxy, and wherein any heterocyclyl group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the R¹ substituents defined hereinbefore which comprises a CH₂ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino.

R¹ is a non-aromatic saturated or partially saturated 3- to 10-membered monocyclic or bicyclic ring or a 5- to 7-membered monocyclic ring each with up to five heteroatoms selected from oxygen, nitrogen and sulphur, and wherein any group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the R¹ substituents defined hereinbefore which comprises a CH₂ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino.

R¹ is heterocyclyl or heterocyclyloxy, and wherein any heterocyclyl group in a R¹ substituent may optionally bear 1 or 2 substituents selected from (1-6C)alkyl, (3-6C)cycloalkyl-(1-6C)alkyl, (1-6C)alkoxycarbonyl, (1-6C)alkoxycarbonyl-(1-6C)alkyl and hydroxy-(1-6C)alkyl.

R¹ is morpholinyl, thiomorpholinyl, piperidinyl, piperidinyloxy, homopiperidinyl, piperazinyl or homopiperazinyl, and wherein any group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the $R^1$ substituents defined hereinbefore which comprises a $CH_2$ group which is attached to 2 carbon atoms or a $CH_3$ group which is attached to a carbon atom may optionally bear on each said $CH_2$ or $CH_3$ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino.

$R^1$ is morpholinyl, thiomorpholinyl, piperidinyl, piperidinyloxy, homopiperidinyl, piperazinyl or homopiperazinyl, and wherein any heterocyclyl group in a $R^1$ substituent may optionally bear 1 or 2 substituents selected from (1-6C)alkyl, (3-6C)cycloalkyl-(1-6C)alkyl, (1-6C)alkoxycarbonyl, (1-6C)alkoxycarbonyl-(1-6C)alkyl and hydroxy-(1-6C)alkyl.

$R^1$ is piperidinyl, piperidinyloxy, homopiperidinyl, piperazinyl or homopiperazinyl, and wherein any group in a $R^1$ substituent may optionally bear 1 or 2 substituents selected from methyl, ethyl, propyl, isopropyl, cyclopropylmethyl, tert-butoxycarbonyl, tert-butoxycarbonylmethyl and 2-hydroxyethyl.

$R^1$ is 4-methylpiperazin-1yl.

$R^2$ is halogeno, trifluoromethyl or (1-6C)alkyl.

$R^2$ is trifluoromethyl or (1-6C)alkyl.

$R^2$ is (1-6C)alkyl. $R^2$ is trifluoromethyl or methyl.

$R^2$ is methyl.

$R^3$ is hydrogen, halogeno or (1-6C)alkyl;

$R^3$ is hydrogen or halogeno.

$R^3$ is hydrogen or chloro.

$R^3$ is chloro.

$R^3$ is hydrogen.

$R^4$ is isoxazolyl, and $R^4$ may be optionally substituted by one or more substituents selected from halogeno, hydroxy, amino, (1-6C)alkyl, (2-6C)alkenyl, (2-6C)alkynyl, (1-6C)alkoxy, (1-6C)alkylamino and di-[(1-6C)alkyl]amino.

$R^4$ is isoxazolyl, and $R^4$ may be optionally substituted by one or more substituents selected from halogeno, (1-6C)alkyl, (1-6C)alkoxy, (1-6C)alkylamino and di-[(1-6C)alkyl]amino.

$R^4$ is isoxazolyl, and $R^4$ may be optionally substituted by one or more substituents selected from halogeno and (1-6C)alkyl.

$R^4$ is isoxazol-3-yl or isoxazol-5-yl, and $R^4$ may be optionally substituted by one or more substituents selected from halogeno and (1-6C)alkyl.

$R^4$ is isoxazol-3-yl or isoxazol-5-yl.

Particular novel compounds of the invention include, for example, amide derivatives of the Formula I, or pharmaceutically-acceptable salts thereof, wherein:—

(a) m is 1;

$R^1$ is heterocyclyl, heterocyclyl-(1-6C)alkyl, heterocyclyloxy, heterocyclyl-(1-6C)alkoxy or heterocyclylamino, and wherein any heterocyclyl group in a $R^1$ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the $R^1$ substituents defined hereinbefore which comprises a $CH_2$ group which is attached to 2 carbon atoms or a $CH_3$ group which is attached to a carbon atom may optionally bear on each said $CH_2$ or $CH_3$ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino;

$R^2$ is trifluoromethyl or methyl;

$R^3$ is hydrogen or chloro; and $R^4$ is isoxazolyl, and $R^4$ may be optionally substituted by one or more substituents selected from halogeno, hydroxy, amino, (1-6C)alkyl, (2-6C)alkenyl, (2-6C)alkynyl, (1-6C)alkoxy, (1-6C)alkylamino and di-[(1-6C)alkyl]amino.

(b) m is 1;

$R^1$ is heterocyclyl or heterocyclyloxy, and wherein any heterocyclyl group in a $R^1$ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the $R^1$ substituents defined hereinbefore which comprises a $CH_2$ group which is attached to 2 carbon atoms or a $CH_3$ group which is attached to a carbon atom may optionally bear on each said $CH_2$ or $CH_3$ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino;

$R^2$ is methyl;

$R^3$ is hydrogen; and $R^4$ is isoxazolyl, and $R^4$ may be optionally substituted by one or more substituents selected from halogeno and (1-6C)alkyl.

(c) m is 1;

$R^1$ is heterocyclyl or heterocyclyloxy, and wherein any heterocyclyl group in a $R^1$ substituent may optionally bear 1 or 2 substituents selected from (1-6C)alkyl, (3-6C)cycloalkyl-(1-6C)alkyl, (1-6C)alkoxycarbonyl, (1-6C)alkoxycarbonyl-(1-6C)alkyl and hydroxy-(1-6C)alkyl;

$R^2$ is methyl;

$R^3$ is hydrogen; and $R^4$ is isoxazol-3-yl or isoxazol-5-yl (d) m is 1;

$R^1$ is morpholinyl, thiomorpholinyl, piperidinyl, piperidinyloxy, homopiperidinyl, piperazinyl or homopiperazinyl, and wherein any heterocyclyl group in a $R^1$ substituent may optionally bear 1 or 2 substituents selected from (1-6C)alkyl, (3-6C)cycloalkyl-(1-6C)alkyl, (1-6C)alkoxycarbonyl, (1-6C)alkoxycarbonyl-(1-6C)alkyl and hydroxy-(1-6C)alkyl.

$R^2$ is methyl;

$R^3$ is hydrogen; and $R^4$ is isoxazol-3-yl or isoxazol-5-yl

A particular preferred compound of the invention is, for example:—

N-isoxazol-3-yl-4-methyl-3-[6-(4-methylpiperazin-1-yl)-4-oxoquinazolin-3(4H)-yl]benzamide;

N-isoxazol-5-yl-4-methyl-3-[6-(4-methylpiperazin-1-yl)-4-oxoquinazolin-3(4H)-yl]benzamide;
3-[6-(4-isopropylpiperazin-1-yl)-4-oxoquinazolin-3(4H)-yl]-N-isoxazol-3-yl-4-methylbenzamide;
3-[6-(4-ethylpiperazin-1-yl)-4-oxoquinazolin-3(4H)-yl]-N-isoxazol-3-yl-4-methylbenzamide;
3-[6-(4-(2-methoxyethyl)piperazin-1-yl)-4-oxoquinazolin-3(4H)-yl]-N-isoxazol-3-yl-4-methylbenzamide;
N-isoxazol-3-yl-4-methyl-3-[4-oxo-6-(2-piperidin-1-ylethoxy)quinazolin-3(4H)-yl]benzamide;
3-[8-cyano-6-(4-methylpiperazin-1-yl)-4-oxoquinazolin-3(4H)-yl]-N-isoxazol-3-yl-4-methylbenzamide;
3-[8-Cyano-6-(4-ethylpiperazin-1-yl)-4-oxoquinazolin-3(4H)-yl]-N-isoxazol-3-yl-4-methylbenzamide;
3-[6-[4-(cyclopropylmethyl)piperazin-1-yl]-4-oxoquinazolin-3(4H)-yl]-N-isoxazol-3-yl-4-methylbenzamide;
4-Methyl-N-(5-methylisoxazol-4-yl)-3-[6-(4-methylpiperazin-1-yl)-4-oxoquinazolin-3(4H)-yl]benzamide;
3-[6-{2-[Isopropyl(methyl)amino]ethoxy}-4-oxoquinazolin-3(4H)-yl]-N-isoxazol-3-yl-4-methylbenzamide;
N-isoxazol-3-yl-4-methyl-3-[4-oxo-6-(2-pyrrolidin-1-ylethoxy)quinazolin-3(4H)-yl]benzamide;
N-isoxazol-3-yl-4-methyl-3-[6-[2-(1,4-oxazepan-4-yl)ethoxy]-4-oxoquinazolin-3(4H)-yl]benzamide;
3-[6-[4-(Cyclobutyl)piperazin-1-yl]-4-oxoquinazolin-3(4H)-yl]-N-isoxazol-3-yl-4-methylbenzamide;
3-[6-{2-[Dimethylamino]ethoxy}-4-oxoquinazolin-3(4H)-yl]-N-isoxazol-3-yl-4-methylbenzamide;
3-[6-{[(3S)-1-Isopropylpyrrolidin-3-yl]oxy}-4-oxoquinazolin-3(4H)-yl]-N-isoxazol-3-yl-4-methylbenzamide; and
N-isoxazol-3-yl-4-methyl-3-[6-(morpholin-4-ylmethyl)-4-oxoquinazolin-3(4H)-yl]benzamide;

or a pharmaceutically-acceptable salt thereof.

Compounds of the Formula I, or a pharmaceutically-acceptable salts thereof, may be prepared by any process known to be applicable to the preparation of chemically-related compounds. Suitable processes are illustrated by, for example, those in WO 00/55153. Such processes, when used to prepare a novel compound of the Formula I are provided as a further feature of the invention and are illustrated by the following representative process variants in which, unless otherwise stated, $R^1$, $R^2$, $R^3$ and $R^4$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) A compound of the Formula I, or a pharmaceutically-acceptable salt thereof, may be prepared by reacting an N-phenyl-2-aminobenzamide of the Formula II

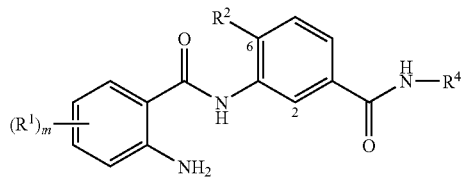

with a carboxylic acid of the Formula III, or a reactive derivative thereof,

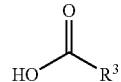

wherein variable groups are as defined hereinbefore and wherein any functional group is protected if necessary, and:
(i) removing any protecting groups; and
(ii) optionally forming a pharmaceutically-acceptable salt.

A suitable reactive derivative of a carboxylic acid of the Formula III is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid with a phenol such as pentafluorophenol, with an ester such as pentafluorophenyl trifluoroacetate or with an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide. A preferred reactive derivative of a carboxylic acid of the Formula III is, for example, an ester of the corresponding ortho acid of the carboxylic acid of the Formula III, for example a trialkyl ester such as a trimethyl or triethyl ester. For a carboxylic acid of the Formula III wherein $R^3$ is hydrogen, a suitable ortho acid ester is triethyl orthoformate and for a carboxylic acid of the Formula III wherein $R^3$ is methyl, a suitable ortho acid ester is triethyl orthoacetate.

The reaction may conveniently be carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene.

The reaction may also conveniently be carried out in the presence of a suitable acid such as, for example, an inorganic or organic acid such as hydrochloric, hydrobromic, sulphuric, acetic, trifluoroacetic, citric or maleic acid.

The reaction is also preferably carried out in a suitable inert solvent or diluent, for example methanol, ethanol, tetrahydrofuran, methylene chloride, 1,2-dimethoxyethane, N,N-dimethylformamide, N,N-dimethylacetamide, N-methylpyrrolidin-2-one, dimethylsulphoxide or acetone, and at a temperature in the range, for example, 0 to 150° C., conveniently at or near 75° C.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, tert-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); aryl lower alkyl groups (for example benzyl, p-methoxybenzyl, o-nitrobenzyl, p-nitrobenzyl, benzhydryl and phthalidyl); tri(lower alkyl) silyl groups (for example trimethylsilyl and tert-butyldimethylsilyl); tri(lower alkyl)silyl lower alkyl groups (for example trimethylsilylethyl); and (2-6C)alkenyl groups (for example allyl and vinylethyl). Methods particularly appropriate for the removal of carboxyl protecting groups include for example acid-, base-, metal- or enzymically-catalysed hydrolysis.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, tert-butyldimethylsilyl) and aryl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example tert-butoxycarbonyl); lower alkenyloxycarbonyl (for example allyloxycarbonyl); aryl lower alkoxycarbonyl groups (for example benzyloxycarbonyl, p-methoxybenzyloxycarbonyl, o-nitrobenzyloxycarbonyl, p-nitrobenzyloxycarbonyl; trialkylsilyl (for example trimethylsilyl and tert-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis for groups such as p-nitrobenzyloxycarbonyl, hydrogenation for groups such as benzyl and photolytically for groups such as o-nitrobenzyloxycarbonyl.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

The N-phenyl-2-aminobenzamide of the Formula II may be prepared by reduction of the corresponding nitro compound of the Formula IV

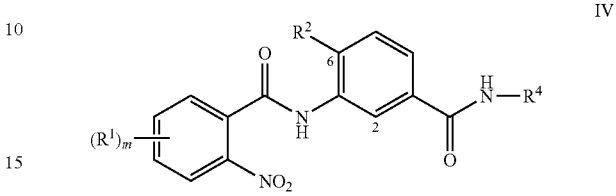

IV

Typical reaction conditions include the use of ammonium formate or hydrogen gas in the presence of a catalyst, for example a metallic catalyst such as palladium-on-carbon. Alternatively a dissolving metal reduction may be carried out, for example using iron in the presence of an acid, for example an inorganic or organic acid such as hydrochloric, hydrobromic, sulphuric or acetic acid. The reaction is conveniently carried out in the presence of an organic solvent (preferably a polar protic solvent) and preferably with heating, for example to about 60° C. Any functional groups are protected and deprotected as necessary.

The nitrobenzene of the Formula IV may be prepared by the reaction of the acid of the Formula V, or a reactive derivative thereof as defined hereinbefore

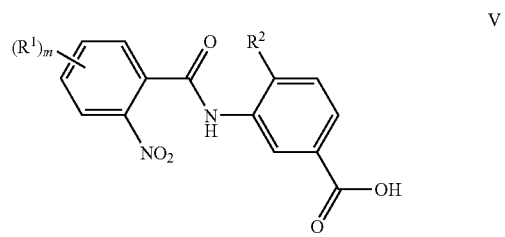

V with a amine of the Formula VI,

VI under standard amide bond forming conditions, wherein variable groups are as defined hereinbefore and wherein any functional group is protected if necessary.

Typical conditions include activating the carboxy group of the compound of Formula V, for example by treatment with a halo reagent (for example oxalyl chloride) to form an acyl halide in an organic solvent at ambient temperature and then reacting the activated compound with the amine of Formula VI. Any functional groups are protected and deprotected as necessary. Conveniently a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

An acid of the Formula V may be prepared by the reaction of a benzoic acid of Formula VII, or an activated derivative thereof as defined hereinbefore,

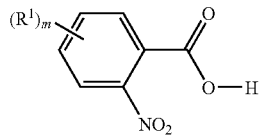

VII with an aniline of Formula VIII

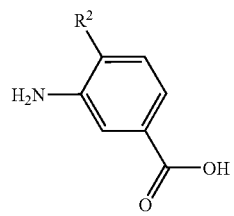

VIII wherein variable groups are as defined hereinbefore and wherein the carboxy group is protected as necessary, and:

(i) removing any protecting groups;

under suitable amide bond forming conditions as defined hereinbefore.

The nitrobenzene of Formula IV may also be prepared by the reaction of a benzoic acid of Formula VII, or an activated derivative thereof as defined hereinbefore, with an aniline of Formula IX

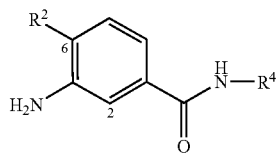

IX under suitable amide bond forming conditions as defined hereinbefore;

(b) A compound of the Formula I or a pharmaceutically-acceptable salt thereof, may be prepared by reacting a carboxylic acid of the Formula X or a reactive derivative thereof as defined hereinbefore,

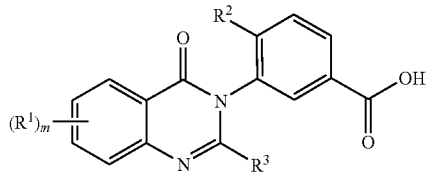

X with a amine of the Formula VI,

VI under standard amide bond forming conditions as defined hereinbefore, wherein variable groups are as defined hereinbefore and wherein any functional group is protected if necessary, and:

(i) removing any protecting groups; and (ii) optionally forming a pharmaceutically-acceptable salt.

The reaction is preferably carried out in the presence of a suitable base as defined hereinbefore The reaction is preferably carried out in a suitable inert solvent or diluent, for example tetrahydrofuran, methylene chloride, 1,2-dimethoxyethane, N,N-dimethylformamide, N,N-dimethylacetamide, N-methylpyrrolidin-2-one, dimethylsulphoxide or acetone, and at a temperature in the range, for example, −78 to 150° C., conveniently at or near ambient temperature.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C. Other typical conditions include activating the carboxy group of the compound of Formula X, for example by treatment with a halo reagent (for example oxalyl or thionyl chloride) to form an acyl halide in an organic solvent at ambient temperature and then reacting the activated compound with the amine of Formula VI.

A carboxylic acid of the Formula X may be prepared by deprotection under standard conditions as defined hereinbefore of the corresponding protected carboxy compound of the Formula XI, wherein P is a carboxy protecting group (such as an ester), as defined hereinbefore. Typically this transformation is achieved using an aqueous solution of sodium hydroxide or anhydrous sodium methoxide in an alcoholic medium, such as methanol in the region of 40-65° C. to give the carboxylate salt. The desired carboxylic acid X is recovered by addition of an aqueous acid, typically dilute hydrochloric acid.

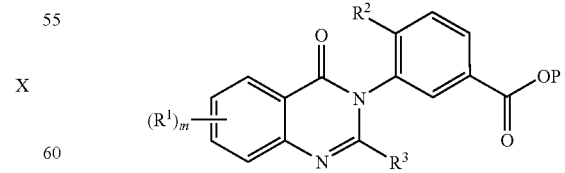

XI

The protected carboxy compound of the Formula XI may be prepared by reacting an N-phenyl-2-aminobenzamide of the Formula XII

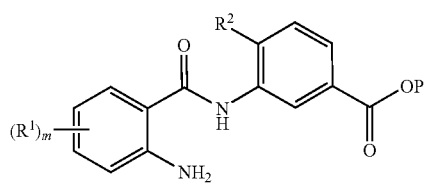

XII with a carboxylic acid of the Formula III, or a reactive derivative thereof,

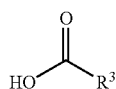

III wherein variable groups are as defined hereinbefore and wherein any functional group is protected if necessary.

The protected carboxy compound of the Formula XI may also be prepared by reacting an aryl bromide of the formula XIII

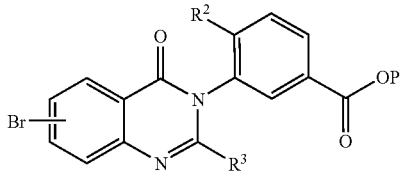

XIII with an $(R^1)_m$-amine under standard amination forming conditions, wherein variable groups are as defined hereinbefore and wherein any functional group is protected if necessary.

Typical conditions include the use of a suitable transition metal catalyst precursor, such as Palladium Acetate in the presence of a chelating bidentate phosphine ligand, such as BINAP with an inorganic base such as cesium carbonate. Conveniently, aromatic solvents such as toluene is used for this transformation at temperature, for example in the region 80 to 110° C., typically at temperature of about 100° C. The transformation may also be effected using the aryl iodides or aryl triflate versions of a compound of the formula XIII.

The Aryl Bromide compound of the Formula XIII may be prepared by reacting a commercially available substituted anthranilic acid derivative of the formula XIV wherein R is hydrogen or (1-6C)alkyl,

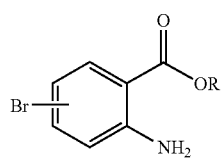

XIV with an aniline of Formula VIII

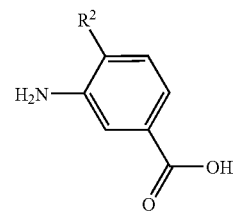

VIII and reacting the resultant compound with a carboxylic acid of the Formula IX, or a reactive derivative thereof,

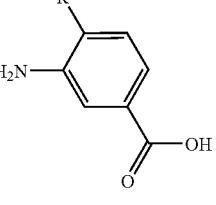

IX wherein variable groups are as defined hereinbefore and wherein any functional group is protected if necessary, and:
   (i) removing any protecting groups; and
   (ii) optionally forming a pharmaceutically-acceptable.

A suitable reactive derivative of a carboxylic acid of the Formula IX is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid with a phenol such as pentafluorophenol, with an ester such as pentafluorophenyl trifluoroacetate or with an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide. A preferred reactive derivative of a carboxylic acid of the Formula IX is, for example, an ester of the corresponding ortho acid of the carboxylic acid of the Formula IX, for example a trialkyl ester such as a trimethyl or triethyl ester. For a carboxylic acid of the Formula IX wherein $R^3$ is hydrogen, a suitable ortho acid ester is triethyl orthoformate and for a carboxylic acid of the Formula IX wherein $R^3$ is methyl, a suitable ortho acid ester is triethyl orthoacetate.

The reaction requires an acid catalyst such as sulphuric, p-toluenesulfonic, formic, benzoic, acetic and trifluoroacetic.

The reaction is also preferably carried out in a suitable inert solvent, for example, ethanol, n-Butanol, 2-Methyl-Butan-2-ol (tert-Amyl alcohol), cyclohexanol, n-butyl acetate, propionitrile, 4-Methyl-2-Pentanone (MIBK), N-methylpyrrolidinone, acetic acid, anisole and toluene at a temperature in the range, for example, 78 to 120° C., conveniently at or near 100° C.

(c) A compound of the Formula I wherein a substituent on $R^1$ or $R^4$ is (1-6C)alkoxy or substituted (1-6C)alkoxy, (1-6C)alkylamino or di-[(1-6C)alkyl]amino may be prepared by the alkylation, conveniently in the presence of a suitable base as defined hereinbefore, of a compound of the Formula I wherein a substituent on $R^1$ or $R^4$ is hydroxy or amino as appropriate.

The reaction is preferably carried out in the presence of a suitable inert solvent or diluent, for example a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 150° C., preferably in the range 20 to 80° C.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1-6C)alkyl chloride, bromide or iodide or a substituted (1-6C)alkyl chloride, bromide or iodide, in the presence of a suitable base as defined hereinbefore, in a suitable inert solvent or diluent as defined hereinbefore and at a temperature in the range, for example, 10 to 140° C., conveniently at or near ambient temperature.

(d) A compound of the Formula I wherein a substituent a substituent on $R^1$ or $R^4$ is amino, (1-6C)alkylamino or di-[(1-6C)alkyl]amino may be prepared by the reaction, conveniently in the presence of a suitable base as defined hereinbefore, of a compound of the Formula I wherein a substituent on $R^1$ or $R^4$ is a suitable leaving group with an appropriate amine.

A suitable leaving group is, for example, a halogeno group such as fluoro, chloro or bromo, a (1-6C)alkanesulphonyloxy group such as methanesulphonyloxy or an arylsulphonyloxy group such as 4-toluenesulphonyloxy.

The reaction is conveniently carried out in the presence of a suitable inert diluent or carrier as defined hereinbefore and at a temperature in the range, for example, 20 to 200° C., conveniently in the range 75 to 150° C.

The following biological assays and Examples serve to illustrate the present invention.

Biological Assays

The following assays can be used to measure the p38 kinase-inhibitory, the TNF-inhibitory and anti-arthritic effects of compounds of the Formula I:

In Vitro Enzyme Assay

The ability test compounds to inhibit the enzyme p38 kinase was assessed. Activity of the test compound against each of the p38α and p38β isoforms of the enzyme was determined.

Human recombinant MKK6 (GenBank Accession Number G1209672) was isolated from Image clone 45578 (*Genomics*, 1996, 33, 151) and utilised to produce protein in the form of a GST fusion protein in a pGEX vector using analogous procedures to those disclosed by J. Han et al, *Journal of Biological Chemistry*, 1996, 271, 2886-2891. p38α (GenBank Accession Number G529039) and p38β (GenBank Accession Number G1469305) were isolated by PCR amplification of human lymphoblastoid cDNA (GenBank Accession Number GM1416) and human foetal brain cDNA [synthesised from mRNA (Clontech, catalogue no. 6525-1) using a Gibco superscript cDNA synthesis kit] respectively using oligonucleotides designed for the 5' and 3' ends of the human p38α and p38β genes using analogous procedures to those described by J. Han et al., *Biochimica et Biophysica Acta*, 1995, 1265, 224-227 and Y. Jiang et al, *Journal of Biological Chemistry*, 1996, 271, 17920-17926.

Both p38 protein isoforms were expressed in *E. coli* in PET vectors. Human recombinant p38α and p38β isoforms were produced as 5' c-myc, 6His tagged proteins. Both MKK6 and the p38 proteins were purified using standard protocols: the GST MKK6 was purified using a glutathione sepharose column and the p38 proteins were purified using nickel chelate columns.

The p38 enzymes were activated prior to use by incubation with MKK6 for 3 hours at 30° C. The unactivated *E. coli*-expressed MKK6 retained sufficient activity to fully activate both isoforms of p38. For p38α, the activation incubate comprised p38α (50 µl of 10 mg/ml), MKK6 (5 µl of 12 mg/ml), 'Kinase buffer' [550 µl; pH 7.4 buffer comprising Tris HCl (50 mM), EGTA (0.1 mM), sodium orthovanadate (0.1 mM) and β-mercaptoethanol (0.1%)], Mg [75 µl of 100 mM Mg $(OCOCH_3)_2$] and ATP (75 µl of 1 mM). The activation incubate for p38β was similar to the above except containing p38β enzyme (82 µl at 3.05 mg/ml) and 518 µl "Kinase buffer". p38α and p38β activation incubates were either used fresh or aliquoted and stored at −80° C.

The test compound was solubilised in DMSO (10 mM) and 1:3 serial dilutions in DMSO carried out in polypropylene plates (Costar 3365). Compound dilutions were then diluted 1:10 in "Kinase buffer" and 10 µl transferred to a microtiter assay plate (Costar 3596). Control wells contained 10 µl (1:10 dilution in kinase buffer) DMSO. 'Kinase Assay Mix' [30 µl; comprising Myelin Basic Protein (Sigma M-1891; 0.5 ml of a 6.66 mg/ml solution in "Kinase buffer"), activated p38α enzyme (3.8 µl) and 'Kinase Buffer' (2.55 ml)] was then added. Control wells on each plate either contained the above "Kinase Assay Mix" (n=6 replicates) or contained "Kinase Assay Mix" in which the activated p38 enzyme was replaced by Kinase buffer (n=6 replicates). 'Labelled ATP' was then added to all wells [10 µl; comprising 50 µM ATP, 5 µCi $^{33}$P ATP (Amersham International cat. no. AH9968) and 50 mM Mg $(OCOCH_3)_2$]. For p38β, 23 µl activated p38β enzyme and "Kinase buffer" (2.53 ml) were included in the "Kinase Assay Mix". The final concentration of test compound was 2.4 µM-0.00 µM (n=2 replicates). Microtiter plates were incubated at ambient temperature (with gentle agitation) for 60 minutes and the reaction stopped by addition of 20% trichloroacetic acid (TCA) (50 µl). The precipitate protein was captured onto filter plates (PerkinElmer 6005174) using a Packard Filtermate harvester (2% TCA wash) which was then dried overnight and 25 µl MICROSCINT O (Packard O6013611) added to each well. Plates were counted on a Top Count scintillation counter. Dose response curves were generated using an in house automated data analysis package and an Origin curve fitting package.

In Vitro Cell-Based Assays (i) PBMC

The ability of a test compound to inhibit TNFα production was assessed by using human peripheral blood mononuclear cells which synthesise and secrete TNFα when stimulated with lipopolysaccharide (LPS).

Peripheral blood mononuclear cells (PBMC) were isolated from heparinised (10 units/ml heparin) human blood by density centrifugation (Lymphoprep™; Nycomed). Mononuclear cells were resuspended in "Culture Medium" [RPMI 1640 medium (Sigma R0883) containing 50 units/ml penicillin, 50 µg/ml streptomycin and 2 mM glutamine] supplemented with 1% heat-inactivated human AB serum (Sigma H-1513)]. Compounds were solubilised in DMSO at a concentration of 20 mM, diluted 1:100 in "culture medium" and serial dilutions carried out in "Culture Medium" containing 1% DMSO. PBMCs ($2.2 \times 10^5$ cells in 160 µl culture medium) were incubated with 20 µl of varying concentrations of test compound (duplicate cultures) or 20 µl culture medium containing 1% DMSO (control wells) for 30 minutes at 37° C. in a humidified (5% $CO_2$/95% air) incubator (Corning 3595; 96 well flat-bottom tissue culture plates). 20 μl lipopolysaccharide [LPS *E. Coli* 0111:B4 (Sigma L-4130), final concentration 0.1 μg/ml] solubilised in "Culture Medium" was added to appropriate wells. 20 μl Culture Medium was added to "medium alone" control wells. Six "LPS alone" and six "medium alone" controls were included on each 96 well plate.

The test compound was tested for TNFα inhibitory activity over a final concentration dose range of 20 μM-0.0001 μM. Each test included a known TNFα inhibitor i.e. the p38 MAPK inhibitor, SB203580 (Lee, J. C., et al (1994) Nature 372 p 739-746). Plates were incubated for 24 hours at 37° C. (humidified incubator) after which 100 μl of the supernatant was removed from each well and stored at −80° C. (96 well round-bottom plates; Corning 3799). TNFα levels were determined in each sample using a human TNFα ELISA (using R&D Systems paired antibodies, MAB610 and BAF210.

$$\% \text{ inhibition} = \frac{(\text{test concentration} - \text{medium alone})}{(LPS \text{ alone} - \text{medium alone})} \times 100$$

(ii) Human Whole Blood

The ability of a test compound to inhibit TNFα production was also assessed in a human whole blood assay. Human whole blood secretes TNFα when stimulated with LPS.

Heparinised (10 units/ml) human blood was obtained from volunteers. 160 μl whole blood was added to 96 well round-bottom plates (Corning 3799). Compounds were solubilised in DMSO at a concentration of 10 mM, diluted 1:100 in "culture medium" [RPMI 1640 medium (Sigma) containing 50 units/ml penicillin, 50 μg/ml streptomycin and 2 mM glutamine] and subsequently serial dilutions were made in culture medium containing 1% DMSO. 20 μl of each test concentration was added to appropriate wells (triplicate cultures)(final concentration dose range of 10 μM-0.0001 μM). 20 μl of RPMI culture medium containing 1% DMSO was added to control wells.

Plates were incubated for 30 minutes at 37° C. (humidified incubator), prior to addition of 20 μl LPS (final concentration 10 μg/ml). Culture medium was added to control wells. Six "LPS alone" and six "medium alone" controls were included on each plate. A known TNFα synthesis/secretion inhibitor was included in each test. Plates were incubated for 6 hours at 37° C. (humidified incubator). Plates were centrifuged (2000 rpm for 10 minutes) and 80 μl plasma removed and stored at −80° C. (Corning 3799 plates). TNFα levels were measured by ELISA using paired antibodies from R&D Systems (catalogue nos. MAB610 and BAF210).

In Vivo Assessment

The ability of a test compound to inhibit TNFα synthesis in vivo was assessed in a rat lipopolysaccharide (LPS)-challenge model. Briefly, compound was dosed orally (100-0.3 mg/kg in 20% DMSO (Sigma D-2650)/60% PEG 400 (Fisher Scientific P/3676/08)/20% sterile de-ionised water; 5 animals per group) to female Wistar Alderley Park (AP) rats (80-100 g) at appropriate timepoints prior to challenge with LPS. Control animals (10 per group) were dosed vehicle alone. LPS (LPS *E. Coli* 0111:B4; Sigma L-4130) was administered intravenously (30 μg in 0.2 ml sterile physiological saline (Phoenix Pharma Ltd). A control group were challenged with 0.2 ml sterile physiological saline. Blood was obtained 60 minutes later from anaesthetised animals and serum isolated after 2 hours incubation at ambient temperature (Sarstedt serum separator 1 ml microtubes, ref 41.1500.005) and centrifugation. Serum samples were stored at −80° C. prior to determination of TNFα content by ELISA (R&D Systems rat TNFα Quantikine kit, catalogue no. SRTA00). % inhibition TNFα calculated as $$100 - [(\text{compound treated} - \text{saline control})/\text{LPS control} - \text{saline control}) \times 100]$$

Test as Anti-Arthritic Agent

Compound was tested for activity in a rat streptococcal cell-wall-induced arthritis model (SCW) [for further information see Carlson, R. P. and Jacobsen, P. B. (1999) Comparison of adjuvant and streptococcal cell-wall-induced arthritis in the rat. In In Vivo Models of Inflammation, eds Morgan, D. W. and Marshall, L. A., Birkhauser Verlag, Basel, Switzerland].

Briefly, female Lewis rats (160-180 g) were sensitised by intra-articular injection of 5 μg streptococcal cell wall (Lee Labs, PG-PS 100P) in 20 μl sterile physiological saline into the left ankle. Responsiveness was assessed 3 days later and animals randomised. Arthritis was induced 21 days after sensitisation (designated day 0) by intravenous injection of 100 μg scw (in 500 μl sterile physiological saline). Compound was dosed orally (50-1 mg/kg once daily) (4 ml/kg) either before (day−1) or after disease onset (day+1) (10 animals per test group; vehicle 0.5% (w/v) HPMC and 0.1% (w/v) polysorbate 80). Control animals (n=10) received vehicle alone. "Non-induced" control animals which were dosed with vehicle were also included (5 animals per group). Animals were weighed on a daily basis from day−1 and ankle diameters measured with Vernier callipers on a daily basis from day−1. At termination on day 6, left hind limbs were removed and fixed in 10% formalin for histological assessment.

Although the pharmacological properties of the compounds of the Formula I vary with structural change as expected, in general a compound of the Formula a gives over 50% inhibition of p38α and/or p38β at concentrations less than 1 μM. No physiologically unacceptable toxicity was observed at the effective dose for compounds tested of the present invention.

According to a further aspect of the invention there is provided a pharmaceutical composition which comprises compound of the Formula I, or a pharmaceutically-acceptable salt thereof, in association with a pharmaceutically-acceptable diluent or carrier.

According to a further aspect of the invention there is provided a pharmaceutical composition for use in the treatment of diseases mediated by cytokines which comprises compound of the Formula I, or a pharmaceutically-acceptable salt thereof, in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent compounded with an appropriate and convenient amount of excipients which may vary from about 5 to about 98 percent by weight of the total composition.

The size of the dose for therapeutic or prophylactic purposes of a compound of the Formula I of the invention will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

According to a further aspect of the invention there is provided a compound of the Formula I, or a pharmaceutically-acceptable salt thereof, for use in a method of treatment of the human or animal body by therapy.

According to a further aspect of the invention there is provided the use of a compound of the Formula I, or a pharmaceutically-acceptable salt thereof, in the manufacture of a medicament.

According to a further aspect of the invention there is provided the use of a compound of the Formula I, or a pharmaceutically-acceptable salt thereof, in the manufacture of a medicament for use in the treatment of medical conditions mediated by cytokines.

In a further aspect the present invention provides a method of treating diseases or medical conditions mediated by cytokines which comprises administering to a warm-blooded animal an effective amount of a compound of the Formula I, or a pharmaceutically-acceptable salt thereof.

In a further aspect the present invention provides a method of treating a disease or medical condition mediated by cytokines which comprises administering to a warm-blooded animal in need thereof a cytokine inhibiting amount of a compound of the Formula I, or a pharmaceutically-acceptable salt thereof.

In a further aspect the present invention provides a method of treating a disease or medical condition mediated by the production or effect of cytokines which comprises administering to a warm-blooded animal in need thereof a cytokine inhibiting amount of a compound of the Formula I, or a pharmaceutically-acceptable salt thereof.

In a further aspect on the invention there is provided a method for inhibiting the production or effect of a cytokine in a warm-blooded animal in need thereof a p38 kinase inhibiting amount of a compound of the Formula I, or a pharmaceutically-acceptable salt thereof.

In a further aspect the present invention provides the use of a compound of the Formula I, or a pharmaceutically-acceptable salt thereof, in the manufacture of a medicament for use in the treatment of diseases or medical conditions mediated by TNF, IL-1, IL-6 or IL-8.

In a further aspect the present invention provides a method of treating diseases or medical conditions mediated by TNF, IL-1, IL-6 or IL-8 which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable salt thereof in the manufacture of a medicament for use in the treatment of diseases or medical conditions mediated by TNF.

In a further aspect the present invention provides a method of treating diseases or medical conditions mediated by TNF which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable salt thereof, in the manufacture of a medicament for use in inhibiting TNF, IL-1, IL-6 or IL-8.

In a further aspect the present invention provides a method of inhibiting TNF, IL-1, IL-6 or IL-8 which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable salt thereof, in the manufacture of a medicament for use in inhibiting TNF.

In a further aspect the present invention provides a method of inhibiting TNF which comprises administering to a warm-blooded animal an effective amount of a compound of the Formula I, or a pharmaceutically-acceptable salt thereof.

In a further aspect the present invention provides a compound of the Formula I, or a pharmaceutically-acceptable salt thereof, in the manufacture of a medicament for use in the treatment of diseases or medical conditions mediated by p38 kinase.

In a further aspect the present invention provides a method of treating diseases or medical conditions mediated by p38 kinase which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable salt thereof, in the manufacture of a medicament for use in the production of a p38 kinase inhibitory effect.

In a further aspect the present invention provides a method of providing a p38 kinase inhibitory effect which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable thereof, in the manufacture of a medicament for use in the treatment of rheumatoid arthritis, asthma, chronic obstructive pulmonary disease, inflammatory bowel disease, multiple sclerosis, AIDS, septic shock, congestive heart failure, ischaemic heart disease or psoriasis.

In a further aspect the present invention provides a method of treating rheumatoid arthritis, asthma, chronic obstructive pulmonary disease, inflammatory bowel disease, multiple sclerosis, AIDS, septic shock, congestive heart failure, ischaemic heart disease or psoriasis which comprises administering to a warm-blooded animal an effective amount of a compound of the Formula I, or a pharmaceutically-acceptable salt thereof.

A compound of the Formula I may be used in combination with other drugs and therapies used in the treatment of disease states which would benefit from the inhibition of cytokines, in particular TNF and IL-1. For example, a compound of the Formula I could be used in combination with drugs and therapies used in the treatment of rheumatoid arthritis, asthma, chronic obstructive pulmonary disease, inflammatory bowel disease, multiple sclerosis, AIDS, septic shock, congestive heart failure, ischaemic heart disease, psoriasis and the other disease states mentioned earlier in this specification.

For example, by virtue of its ability to inhibit cytokines, a compound of the Formula I is of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I of the present invention with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt thereof, in conjunction or admixture with a cyclooxygenase inhibitory non-steroidal anti-inflammatory agent, and a pharmaceutically-acceptable diluent or carrier.

A compound of the Formula I may also be used with anti-inflammatory agents such as an inhibitor of the enzyme 5-lipoxygenase.

A compound of the Formula I may also be used in the treatment of conditions such as rheumatoid arthritis in combination with antiarthritic agents such as gold, methotrexate, steroids and pencillinamine, and in conditions such as osteoarthritis in combination with steroids.

A compound of the Formula I may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

A compound of the Formula I may be used in the treatment of asthma in combination with antiasthmatic agents such as steroids, bronchodilators and leukotriene antagonists.

In particular, for the treatment of the inflammatory diseases rheumatoid arthritis, psoriasis, inflammatory bowel disease, chronic obstructive pulmonary disease, asthma and allergic rhinitis a compound of the present invention may be combined with agents such as TNF-α inhibitors such as anti-TNF monoclonal antibodies (such as Remicade, CDP-870 and $D_2E_7$.) and TNF receptor immunoglobulin molecules (such as Enbrel.reg.), non-selective COX-1/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin), COX-2 inhibitors (such as meloxicam, celecoxib, rofecoxib, valdecoxib and etoricoxib) low dose methotrexate, lefunomide; ciclesonide; hydroxychloroquine, d-penicillamine, auranofin or parenteral or oral gold.

The present invention still further relates to the combination of a compound of the Formula I together with a leukotriene biosynthesis inhibitor, 5-lipoxygenase (5-LO) inhibitor or 5-lipoxygenase activating protein (FLAP) antagonist such as zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY x 1005.

The present invention still further relates to the combination of a compound of the Formula I together with a receptor antagonist for leukotrienes $LTB_4$, $LTC_4$, $LTD_4$, and $LTE_4$ selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the Formula I together with a PDE4 inhibitor including inhibitors of the isoform PDE4D.

The present invention still further relates to the combination of a compound of the Formula I together with a antihistaminic $H_1$ receptor antagonists such as cetirizine, loratadine, desloratadine, fexofenadine, astemizole, azelastine, and chlorpheniramine.

The present invention still further relates to the combination of a compound of the Formula I together with a gastroprotective $H_2$ receptor antagonist.

The present invention still further relates to the combination of a compound of the Formula I together with an $\alpha_1$- and $\alpha_2$-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the Formula I together with anticholinergic agents such as ipratropium bromide; tiotropium bromide; oxitropium bromide; pirenzepine; and telenzepine.

The present invention still further relates to the combination of a compound of the Formula I together with a $\beta_1$- to $\beta_4$-adrenoceptor agonists such as metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the Formula I together with an insulin-like growth factor type I (IGF-1) mimetic.

The present invention still further relates to the combination of a compound of the Formula I together with an inhaled glucocorticoid with reduced systemic side effects, such as prednisone, prednisolone, flunisolide, triamcinolone acetonide, beclomethasone dipropionate, budesonide, fluticasone propionate, and mometasone furoate.

The present invention still further relates to the combination of a compound of the Formula I together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-12.

The present invention still further relates to the combination of a compound of the Formula I together with other modulators of chemokine receptor function such as CCR1, CCR2, CCR2A, CCR2B, CCR3, CCR4, CCR5, CCR6, CCR7, CCR8, CCR9, CCR10 and CCR11 (for the C—C family); CXCR1, CXCR3, CXCR4 and CXCR5 (for the C—X—C family) and $CX_3CR1$ for the C—$X_3$—C family.

The present invention still further relates to the combination of a compound of the Formula I together with antiviral agents such as Viracept, AZT, aciclovir and famciclovir, and antisepsis compounds such as Valant.

The present invention still further relates to the combination of a compound of the Formula I together with cardiovascular agents such as calcium channel blockers, lipid lowering agents such as statins, fibrates, beta-blockers, Ace inhibitors, Angiotensin-2 receptor antagonists and platelet aggregation inhibitors.

The present invention still further relates to the combination of a compound of the Formula I together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metrifonate.

The present invention still further relates to the combination of a compound of the Formula I together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) cathepsins; (vii) MAP kinase inhibitors; (viii) glucose-6 phosphate dehydrogenase inhibitors; (ix) kinin-$B_1$.- and $B_2$.-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) Tachykinin $NK_1$. and $NK_3$. receptor antagonists selected from the group consisting of NKP-608C; SB-233412 (talnetant); and D-4418; (xx) elastase inhibitors selected from the group consisting of UT-77 and ZD-0892; (xxi) TNF? converting enzyme inhibitors (TACE); (xxii) induced nitric oxide synthase inhibitors (iNOS) or (xxiii) chemoattractant receptor-homologous molecule expressed on TH2 cells, (CRTH2 antagonists).

A compound of the Formula I may also be used in combination with osteoporosis agents such as roloxifene, droloxifene, lasofoxifene or fosomax and immunosuppressant agents such as FK-506, rapamycin, cyclosporine, azathioprine, and methotrexate.

A compound of the Formula I may also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc and P2X7 receptor antagonists.

A compound of the Formula I can also be used in combination with existing therapeutic agents for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel (Taxol®); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

If formulated as a fixed dose such combination products employ a compound of the Formula I within the dosage range described herein and the other pharmaceutically-active agent within its approved dosage range. Sequential use is contemplated when a combination formulation is inappropriate.

Although a compound of the Formula I is primarily of value as a therapeutic agent for use in warm-blooded animals (including man), it is also useful whenever it is required to inhibit the effects of cytokines. Thus, it is useful as pharmacological standard for use in the development of new biological tests and in the search for new pharmacological agents.

The invention will now be illustrated in the following non-limiting Example in which, unless otherwise stated:—

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-118 (Art, 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields are given for illustration only and are not necessarily the maximum attainable;

(v) the structure of a compound of the Formula I of the invention was confirmed by nuclear magnetic resonance (NMR) and mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM250 spectrometer operating at a field strength of 250 MHz]; the following abbreviations have been used: s, singlet; d, doublet; t, triplet; q, quartet; m, multiplet; br, broad;

(vi) melting points are uncorrected and were determined using a Mettler SP62 automatic melting point apparatus or an oil-bath apparatus; and (vii) the following abbreviations have been used:—
DMA N,N-dimethylacetamide
DMF N,N-dimethylformamide
DMSO dimethylsulphoxide
THF tetrahydrofuran
HATU O-(7-azabenzotriazol-1-yl)-N,N,N',N'-tetramethyluronium hexafluorophosphate

EXAMPLE 1

N-isoxazol-3-yl-4-methyl-3-[6-(4-methylpiperazin-1-yl)-4-oxoquinazolin-3(4H)-yl]benzamide Phosphorus oxychloride (0.11 ml) was added to a mixture of 4-methyl-3-[6-(4-methylpiperazin-1-yl)-4-oxoquinazolin-3(4H)-yl]benzoic acid (0.30 g), 3-aminoisoxazole (0.12 ml) and pyridine (5 ml) and the resultant suspension was heated to 120° C. for 5 minutes in a microwave (Personal Chemistry Emrys Optimizer with 300 W magnetron). The mixture was evaporated. The residue was partitioned between ethyl acetate and saturated $NaHCO_3$ solution. The organic phase was dried (magnesium sulphate), evaporated and the residue purified by column chromatography on a silica column using initially methylene chloride and then a 9:1 mixture of methylene chloride and methanol as eluent. There was thus obtained the title compound (0.14 g); NMR Spectrum: (DMSOd$_6$) 2.19 (s, 3H), 2.24 (s, 3H), 2.49 (m, 4H), 3.29 (m, 4H), 7.06 (d, 1H), 7.50 (d, 1H), 7.63 (m, 3H), 8.09 (m, 2H), 8.13 (s, 1H), 8.85 (d, 1H), 11.46 (s, 1H); Mass Spectrum: M+H$^+$ 445.

The 4-methyl-3-[6-(4-methylpiperazin-1-yl)-4-oxoquinazolin-3(4H)-yl]benzoic acid used for the starting material was prepared as follows:—

A) To a stirred solution of methyl 5-bromo-2-aminobenzoate (10.0 g) and methyl 3-amino-4-methylbenzoate (7.90 g) in toluene (100 ml) at 50° C. were added triethylorthoformate (8.12 ml) and glacial acetic acid (2.50 ml). The mixture was heated to reflux for 16 hours. The alcohol by-products were distilled using Dean-stark conditions and the reaction cooled room temperature. The resultant solid was collected by filtration, washed with toluene (2×20 ml) and dried in vacuo at 40° C. to give the methyl 3-(6-bromo-4-oxoquinazolin-3(4H)-yl)-4-methylbenzoate as a white solid (13.1 g); NMR Spectrum: (DMSOd$_6$) 2.16 (s, 3H), 3.85 (s, 3H), 7.60 (d, 1H), 7.71 (d, 1H), 8.01 (m, 3H), 8.26 (s, 1H), 8.34 (s, 1H); Mass Spectrum: M+H$^+$ 373.

B) To a stirred suspension of methyl 3-(6-bromo-4-oxoquinazolin-3(4H)-yl)-4-methylbenzoate (15.0 g), $Cs_2CO_3$ (26.2 g), racemic 2,2'-bis(diphenylphosphino)-1,1'-binaphthyl (1.88 g), palladium acetate (0.46 g) in anhydrous toluene (150 ml) at ambient temperature was added N-methyl piperazine (5.99 ml). The mixture was heated to 100° C. and stirred for 16 hours. Inorganic solids were removed via a hot filtration and the filtrate was allowed to cool to room temperature with stirring to crystallise the product. The mixture was stirred for 16 hours and the solid isolated by filtration, washed with toluene (3×10 ml) and dried in vacuo at 40° C. to give the title compound as a yellow solid (8.44 g); NMR Spectrum: (DMSOd$_6$): 2.15 (s, 3H), 2.23 (s, 3H), 2.48 (m, 4H), 3.29 (m, 4H), 3.85 (s, 3H), 7.46 (m, 1H), 7.58 (m, 3H), 7.98 (m, 2H), 8.07 (s, 1H); Mass Spectrum: M+H$^+$ 393.

C) To a stirred suspension of methyl 4-methyl-3-[6-(4-methylpiperazin-1-yl)-4-oxoquinazolin-3(4H)-yl]benzoate (0.5 g) in methanol (5 ml) at 65° C. was added 1N NaOH (1.6 ml) and was stirred at 65° C. for 30 minutes. The mixture was acidified by addition of 1N HCl (1.6 ml) over 5 minutes and the reaction mixture cooled to room temperature over 1 hour and stirred for a further 30 minutes. The resultant solid was isolated by filtration, washed with water (2 mL), methanol/water (1:1, 2 ml), methanol (2×2 mL) and dried in vacuo at 40° C. to give the title compound as an off-white solid (0.4 g); NMR Spectrum: (DMSOd$_6$) 2.14 (s, 3H), 2.78 (s, 3H), 3.25 (m, 8H), 7.57 (m, 2H), 7.68 (s, 2H), 7.91 (m, 1H), 7.98 (m, 1H), 8.12 (s, 1H); Mass Spectrum: M+H$^+$ 379.

EXAMPLE 2

N-isoxazol-5-yl-4-methyl-3-[6-(4-methylpiperazin-1-yl)-4-oxoquinazolin-3(4H)-yl]benzamide To a stirred slurry of 4-methyl-3-[6-(4-methylpiperazin-1-yl)-4-oxoquinazolin-3(4H)-yl]benzoic acid (0.3 g) and DMF (0.05 ml) in methylene chloride (30 ml) at 35° C. was added thionyl chloride (0.3 ml). The resultant yellow solution was stirred at 45° C. for 1.5 hours. The reaction mixture was concentrated to give a yellow/orange solid. The solid was stirred in methylene chloride (30 ml) at room temperature with 5-aminoisoxazole (0.11 g) and pyridine (0.2 ml) for 18 hours. The reaction mixture was washed with saturated NaHCO$_3$ solution, brine and concentrated. The residue was purified by column chromatography on a silica column using initially methylene chloride and then a 9:1 mixture of methylene chloride and methanol as eluent. There was thus obtained the title compound (70 mg); NMR Spectrum: (DMSOd$_6$) 2.19 (s, 3H), 2.25 (s, 3H), 2.49 (m, 4H), 3.30 (m, 4H), 6.43 (d, 1H), 7.50 (d, 1H), 7.62 (s, 1H), 7.65 (m, 2H), 8.08 (s, 1H), 8.10 (m, 1H), 8.13 (s, 1H), 8.50 (d, 1H), 12.04 (s, 1H); Mass Spectrum: M+H$^+$ 444.

The 5-aminoisoxazole used as starting material was prepared as follows:—

A 50% w/w solution of hydroxylamine in water (6.6 ml) and 3-methoxyacrylonitrile (8.39 ml) were heated at 80° C. for 3 hours. The reaction mixture was cooled to room temperature and extracted with diethyl ether. The combined organic layers were washed with brine, dried (magnesium sulphate) and concentrated to a brown oil which solidified on standing to give the title compound (3.87 g); NMR Spectrum: (DMSOd$_6$) 4.88 (d, 1H), 6.60 (s, 2H), 7.97 (d, 1H); Mass Spectrum: M$^+$ 83.

EXAMPLE 3

3-[6-(4-isopropylpiperazin-1-yl)-4-oxoquinazolin-3(4H)-yl]-N-isoxazol-3-yl-4-methylbenzamide To a stirred slurry of 4-methyl-3-[6-(4-isopropylpiperazin-1-yl)-4-oxoquinazolin-3(4H)-yl]benzoic acid (0.2 g) and DMF (0.05 ml) in methylene chloride (4 ml) at 35° C. was added thionyl chloride (0.20 ml). The resultant green solution was stirred at 40° C. for 18 hours. The reaction mixture was concentrated to give an orange/brown solid. The solid was stirred in methylene chloride (4 ml) at room temperature and 3-aminoisoxazole (0.15 ml) and N,N-diisopropylethylamine (0.26 ml) was added, stirred for 1.5 hours and concentrated. The resultant oil was partitioned between ethyl acetate and saturated NaHCO$_3$ solution. The aqueous layer was separated and the organic layer washed with brine (5 ml). The organic phase was concentrated to give an orange/brown solid. The residue was purified by column chromatography on a silica column using a 9:1 mixture of ethyl acetate and methanol as eluent to give the title compound as a yellow solid (50 mg); NMR Spectrum: (DMSOd$_6$) 1.04 (d, 6H), 2.18 (s, 3H), 2.62 (m, 4H), 2.68 (m, 1H), 3.28 (m, 4H), 7.05 (s, 1H), 7.49 (s, 1H), 7.66 (m, 3H), 8.08 (m, 2H), 8.12 (s, 1H), 8.86 (s, 1H), 11.47 (s, 1H); Mass Spectrum: M+H$^+$ 473.

The 4-methyl-3-[6-(4-isopropylpiperazin-1-yl)-4-oxoquinazolin-3(4H)-yl]benzoic acid used for the starting material was prepared as follows:—

5-Fluoro-2-nitrobenzoic acid (22.2 g) was suspended in methylene chloride (200 ml) and cooled to 0° C. To this suspension was added oxalyl chloride (21 ml) dropwise followed by DMF (1 drop). The reaction mixture was warmed to room temperature and stirred for 4 hours. The reaction mixture was evaporated to dryness and redissolved in methylene chloride (200 ml). To this solution was added methyl-3-amino-4-methylbenzoate (16.5 g) and N,N-diisopropylethylamine (42 ml) in portions. The reaction was stirred at room temperature for 16 hours and then concentrated. The residue was redissolved in 2N HCl (200 ml) and extracted with ethyl acetate. The organic layers were pooled, washed with 2N HCl, saturated NaHCO$_3$ solution, brine, dried (magnesium sulphate) and evaporated in vacuo. The residue was dissolved in methylene chloride (600 ml) and poured into iso-hexane (2 L). The resultant solid was collected by filtration and air dried to give methyl 3-[(5-fluoro-2-nitrobenzoyl)amino]-4-methylbenzoate as a cream solid (18.1 g); NMR Spectrum: (DMSOd$_6$) 2.18 (3H, s), 3.85 (3H, s), 7.41 (1H, d), 7.60 (1H, m), 7.75 (1H, m), 7.83 (1H, m), 8.16 (1H, d), 8.28 (1H, m), 10.26 (1H, s); Mass Spectrum: M−H$^+$ 331.

To a solution of methyl 3-[(5-fluoro-2-nitrobenzoyl)amino]-4-methylbenzoate (8 g) in DMSO (24 ml) was added N-isopropylpiperazine (3.4 g) and N,N-diisopropylethylamine (4.7 ml) and the reaction stirred at room temperature for 6 hours. Water (200 ml) was added and the resultant solid collected by filtration, washed with water (×3) and dried in vacuo at 50° C. for 16 hours to yield methyl 4-methyl-3-{[5-(4-isopropylpiperazin-1-yl)-2-nitrobenzoyl]amino}benzoate as a yellow solid (10.7 g); NMR Spectrum: (DMSOd$_6$) 0.99 (d, 6H), 2.34 (s, 3H), 2.55 (m, 4H), 2.71 (m, 1H), 3.50 (m, 4H), 3.85 (s, 3H), 7.07 (m, 2H), 7.39 (d, 1H), 7.71 (m, 1H), 8.06 (d, 1H), 8.20 (m, 1H), 9.96 (s, 1H); Mass Spectrum: M+H$^+$ 441.

A suspension of methyl 4-methyl-3-{[5-(4-isopropylpiperazin-1-yl)-2-nitrobenzoyl]amino}benzoate (10.7 g) and 10% palladium on carbon (0.3 g) in ethanol (200 ml) was agitated under a hydrogen atmosphere for 16 hours. The reaction mixture was filtered through diatomaceous earth (Celite®) and was concentrated to c.a. 100 ml. To this solution was added triethylorthoformate (4 ml) and glacial acetic acid (0.35 ml) and the mixture was stirred at 80° C. for 16 hours. The reaction mixture was evaporated, redissolved in ethyl acetate, washed with saturated NaHCO$_3$ solution. The organic phase was dried (magnesium sulphate) and evaporated to give methyl 4-methyl-3-[6-(4-isopropylpiperazin-1-yl)-4-oxoquinazolin-3(4H)-yl]benzoate as a foam (7.57 g); NMR Spectrum: (DMSOd$_6$) 1.00 (d, 6H), 2.15 (s, 3H), 2.59 (m, 4H), 2.68 (m, 1H), 3.24 (m, 4H), 3.85 (s, 3H), 7.45 (d, 1H), 7.60 (m, 3H), 7.95 (m, 1H), 8.00 (m, 1H), 8.05 (d, 1H); Mass Spectrum: M+H$^+$ 421.

Methyl 4-methyl-3-[6-(4-isopropylpiperazin-1-yl)-4-oxoquinazolin-3(4H)-yl]benzoate 7.56 g) was dissolved in a mixture of methanol (135 ml) and water (45 ml). 2N NaOH (36 ml) added and stirred at room temperature for 1 hour. The pH was adjusted to 2-3 using 2N HCl and the solvent evaporated in vacuo. The oil was triturated with a mixture of ethyl acetate (100 ml) and iso-hexane (100 ml) and the solid collected by filtration and dried under vacuum at 40° C. for 16 hours to give 4-methyl-3-[6-(4-isopropylpiperazin-1-yl)-4-oxoquinazolin-3(4H)-yl]benzoic acid (9.9 g); NMR Spectrum:

(DMSOd$_6$) 1.33 (d, 6H), 2.14 (s, 3H), 3.15 (m, 2H), 3.46 (m, 5H), 3.98 (m, 2H), 7.55 (m, 2H), 7.68 (m, 2H), 7.89 (m, 1H), 7.98 (m, 1H), 8.18 (t, 1H), 11.56 (s, 1H); Mass Spectrum: M+H$^+$ 407.

EXAMPLE 4

3-[6-(4-ethylpiperazin-1-yl)-4-oxoquinazolin-3(4H)-yl]-N-isoxazol-3-yl-4-methylbenzamide A) To a stirred slurry of 4-methyl-3-[6-(4-ethylpiperazin-1-yl)-4-oxoquinazolin-3(4H)-yl]benzoic acid (0.19 g) and DMF (0.05 ml) in methylene chloride (4 ml) at 35° C. was added thionyl chloride (0.18 ml). The resultant green solution was stirred at 35° C. for 1.5 hours. The reaction mixture was concentrated to give yellow foam. The solid was stirred in methylene chloride (4 ml) at room temperature and 3-aminoisoxazole (0.15 ml) and N,N-diisopropylethylamine (0.25 ml) was added, stirred for 1.5 hours and concentrated. The resultant oil was partitioned between ethyl acetate and a saturated NaHCO$_3$ solution. The aqueous layer was separated and the organic layer washed with brine (5 ml). The organic phase concentrated to give an off-white solid. The solid was triturated with ethyl acetate and collected by filtration to give the title compound as an off-white solid (85 mg); NMR Spectrum: (DMSOd$_6$) 1.05 (3H, t), 2.18 (3H, s), 2.41 (2H, m), 2.55 (4H, m), 3.29 (4H, m), 7.05 (1H, s), 7.50 (1H, s), 7.62 (3H, m), 8.07 (2H, m), 8.13 (1H, s), 8.87 (1H, s), 11.47 (1H, s); Mass Spectrum: M+H$^+$ 459.

The 4-methyl-3-[6-(4-ethylpiperazin-1-yl)-4-oxoquinazolin-3(4H)-yl]benzoic acid used for the starting material was prepared as follows:—

Using an analogous procedure to that described paragraph (B) in the portion of Example 1 which is concerned with the preparation of starting material N-ethylpiperazine was reacted with methyl 3-(6-bromo-4-oxoquinazolin-3(4H)-yl)-4-methylbenzoate to give methyl 4-methyl-3-[6-(4-ethylpiperazin-1-yl)-4-oxoquinazolin-3(4H)-yl]benzoate; NMR Spectrum: (DMSOd$_6$) 1.05 (t, 3H), 2.17 (s, 3H), 2.40 (m, 2H), 2.53 (m, 4H), 3.29 (m, 4H), 3.87 (s, 3H), 7.48 (s, 1H), 7.63 (m, 3H), 7.97 (s, 1H), 8.02 (d, 1H), 8.10 (d, 1H); Mass Spectrum: M+H$^+$ 407.

Using an analogous procedure to that described paragraph (C) in the portion of Example 1 which is concerned with the preparation of starting material methyl 4-methyl-3-[6-(4-ethylpiperazin-1-yl)-4-oxoquinazolin-3(4H)-yl]benzoate was hydrolysed with 1N NaOH to give 4-methyl-3-[6-(4-ethylpiperazin-1-yl)-4-oxoquinazolin-3(4H)-yl]benzoic acid; NMR Spectrum: (DMSOd$_6$) 1.30 (t, 3H), 2.16 (s, 3H), 3.20 (m, 6H), 3.59 (d, 2H), 4.03 (d, 2H), 7.60 (m, 2H), 7.71 (m, 2H), 7.93 (s, 1H), 8.01 (d, 1H), 8.15 (s, 1H), 10.48 (s, 1H), 13.11 (s, 1H); Mass Spectrum: M+H$^+$ 393.

EXAMPLE 5

3-[6-(4-(2-methoxyethyl)piperazin-1-yl)-4-oxoquinazolin-3(4H)-yl]-N-isoxazol-3-yl-4-methylbenzamide Using an analogous procedure to that described paragraph (A) in the portion of Example 4, 4-methyl-3-[6-(4-(2-methoxyethyl)piperazin-1-yl)-4-oxoquinazolin-3(4H)-yl]benzoic acid was reacted with 3-aminoisoxazole to give 3-[6-(4-(2-methoxyethyl)piperazin-1-yl)-4-oxoquinazolin-3(4H)-yl]-N-isoxazol-3-yl-4-methylbenzamide; NMR Spectrum: (DMSOd$_6$) 2.18 (s, 3H), 2.58 (m, 6H), 3.26 (m, 7H), 3.47 (t, 2H), 7.05 (s, 1H), 7.50 (s, 1H), 7.66 (m, 3H), 8.10 (m, 2H), 8.13 (s, 1H), 8.87 (s, 1H), 11.48 (s, 1H); Mass Spectrum: M+H$^+$ 489.

The 4-methyl-3-[6-(4-(2-methoxyethyl)piperazin-1-yl)-4-oxoquinazolin-3(4H)-yl]benzoic acid used for the starting material was prepared as follows:—

Using an analogous procedure to that described paragraph (B) in the portion of Example 1 which is concerned with the preparation of starting material N-(2-methoxyethyl)piperazine was reacted with methyl 3-(6-bromo-4-oxoquinazolin-3(4H)-yl)-4-methylbenzoate to give methyl 4-methyl-3-[6-(4-(2-methoxyethyl)piperazin-1-yl)-4-oxoquinazolin-3(4H)-yl]benzoate; NMR Spectrum: (DMSOd$_6$) 2.18 (s, 3H), 2.55 (t, 2H), 2.60 (m, 4H), 3.25 (s, 3H), 3.27 (m, 4H), 3.50 (t, 2H), 3.88 (s, 3H), 7.47 (s, 1H), 7.62 (m, 3H), 7.97 (s, 1H), 8.01 (m, 1H), 8.09 (s, 1H); Mass Spectrum: M+H$^+$ 437.

Using an analogous procedure to that described paragraph (C) in the portion of Example 1 which is concerned with the preparation of starting material methyl 4-methyl-3-[6-(4-(2-methoxyethyl)piperazin-1-yl)-4-oxoquinazolin-3(4H)-yl]benzoate was hydrolysed with 1N NaOH to give 4-methyl-3-[6-(4-(2-methoxyethyl)piperazin-1-yl)-4-oxoquinazolin-3(4H)-yl]benzoic acid; NMR Spectrum: (DMSOd$_6$) 2.16 (s, 3H), 3.30 (m, 9H), 3.60 (m, 2H), 3.80 (m, 2H), 4.00 (m, 2H), 7.58 (m, 2H), 7.69 (m, 2H), 7.93 (s, 1H), 8.00 (d, 1H), 8.16 (s, 1H), 11.07 (s, 1H), 13.10 (s, 1H); Mass Spectrum: M+H$^+$ 423.

EXAMPLE 6

N-isoxazol-3-yl-4-methyl-3-[4-oxo-6-(2-piperidin-1-ylethoxy)quinazolin-3(4H)-yl]benzamide To a stirred slurry of 4-methyl-3-[4-oxo-6-(2-piperidin-1-ylethoxy)quinazolin-3(4H)-yl]benzoic acid (0.13 g) and DMF (0.05 ml) in methylene chloride (10 ml) at 40° C. was added thionyl chloride (0.11 ml). The resultant solution was stirred at 40° C. for 1 hour. The reaction mixture was concentrated and the resultant solid was redissolved in methylene chloride (10 ml), to this was added 3-aminoisoxazole (0.036 ml) and pyridine (0.08 ml) and stirred for 1 hour. The solution was washed with saturated NaHCO$_3$ solution, concentrated and azetroped with toluene to yield a yellow solid. The solid was resuspended in ethyl acetate and the precipitate removed by filtration. The filtrate was diluted with iso-hexane which resulted in precipitation of a pale yellow solid which was collected by filtration and air dried to give the title compound (31 mg); NMR Spectrum: (DMSOd$_6$) 1.38 (m, 6H), 2.17 (s, 3H), 2.55 (m, 4H), 2.79 (m, 2H), 4.20 (m, 2H), 7.03 (s, 1H), 7.52 (m, 1H), 7.58 (m, 2H), 7.71 (d, 1H), 8.08 (m, 2H), 8.22 (s, 1H), 8.83 (s, 1H), 11.43 (s, 1H); Mass Spectrum: M+H$^+$ 474.

The 4-methyl-3-[4-oxo-6-(2-piperidin-1-ylethoxy)quinazolin-3(4H)-yl]benzoic acid used for the starting material was prepared as follows:—

A suspension of 2-amino-5-methoxybenzoic acid (18.7 g) in toluene (250 ml) was added triethylorthoformate (19.6 ml) and acetic acid (0.64 ml) and heated at 110° C. for 3 hours when methyl-3-amino-4-methylbenzoate (16.7 g) was added and heating continued for a further 16 hours at 110° C. The reaction mixture was cooled to room temperature and diluted with ethyl acetate. The organic phase was washed with 1N NaOH and 1N HCl. The organic phase was left to stand for 54 hours which resulted in crystallisation of a solid which was collected by filtration and air dried to give methyl 3-(6-methoxy-4-oxoquinazolin-3(4H)-yl)-4-methylbenzoate (9.3 g); NMR Spectrum: (DMSOd$_6$) 2.18 (s, 3H), 3.84 (s, 3H), 3.92 (s, 3H), 7.28 (m, 1H), 7.59 (m, 2H), 7.73 (d, 1H), 7.93 (s, 1H), 7.98 (m, 1H), 8.19 (s, 1H); Mass Spectrum: M+H$^+$ 325.

To a stirred suspension of methyl 3-(6-methoxy-4-oxo-quinazolin-3(4H)-yl)-4-methylbenzoate (19.3 g) in a mixture of methanol (650 ml) and water (150 ml) was added 2N NaOH (89 ml) and heated to 70° C. until a clear solution was formed at which point the heating stopped. Stirring was continued for a further 1.5 hours. The pH was adjusted to pH~1 with 1N HCl and the resultant solid collected by filtration. The solid was dried in vacuo for 16 hours to yield 3-(6-methoxy-4-oxoquinazolin-3(4H)-yl)-4-methylbenzoic acid as a white solid (17.8 g); NMR Spectrum: (DMSOd$_6$) 2.15 (s, 3H), 3.88 (s, 3H), 7.49 (m, 1H), 7.57 (m, 2H), 7.71 (d, 1H), 7.93 (s, 1H), 7.98 (m, 1H), 8.20 (s, 1H); Mass Spectrum: M+H$^+$ 311.

To a suspension of 3-(6-methoxy-4-oxoquinazolin-3(4H)-yl)-4-methylbenzoic acid (8 g) in 2,4,6-collidine (80 ml) was added LiI (6.2 g) and heated to 195° C. for 54 hours. The reaction mixture was cooled to room temperature and diluted with ethyl acetate. The organic phase was washed with water. The aqueous phase was acidified to pH~1 with 1N HCl and the resultant solid collected by filtration. The solid was dried in vacuo at 60° C. to yield 3-(6-hydroxy-4-oxoquinazolin-3(4H)-yl)-4-methylbenzoic acid (7.2 g); NMR Spectrum: (DMSOd$_6$) 2.14 (s, 3H), 7.33 (m, 1H), 7.48 (d, 1H), 7.56 (d, 1H), 7.62 (d, 1H), 7.91 (s, 1H), 7.97 (d, 1H), 8.12 (s, 1H); Mass Spectrum: M+H$^+$ 297.

To a suspension of 3-(6-hydroxy-4-oxoquinazolin-3(4H)-yl)-4-methylbenzoic acid (7.2 g) in DMF (150 ml) was added K$_2$CO$_3$ (33 g) and 1-bromo-2-chloroethane (12 ml) and heated to 50° C. for 2 hours. 2N NaOH (24 ml) was added and the solution heated to 40° C. for a further 16 hours. The pH was adjusted to pH~1 with 1N HCl and the resultant solid collected by filtration. The solid was washed with methylene chloride, methanol and dried in vacuo to yield 3-[6-(2-chloroethoxy)-4-oxoquinazolin-3(4H)-yl]-4-methylbenzoic acid (9.1 g); NMR Spectrum: (DMSOd$_6$) 2.14 (s, 3H), 3.98 (m, 2H), 4.40 (m, 2H), 7.55 (m, 3H), 7.72 (d, 1H), 7.93 (s, 1H), 7.98 (d, 1H), 8.19 (s, 1H); Mass Spectrum: M+H$^+$ 359.

To a stirred solution of 3-[6-(2-chloroethoxy)-4-oxoquinazolin-3(4H)-yl]-4-methylbenzoic acid (0.27 g), piperidine (0.3 ml), N,N-diisopropylethylamine (0.53 ml) and KI (0.25 g) in DMA (2 ml) was heated to 120° C. for 30 minutes in a microwave (Personal Chemistry Emrys Optimizer with 300 W magnetron). The reaction mixture was diluted with methylene chloride (20 ml), CombiZorb isocyanate resin (loading 1.03 mmol/g from Agilent) (5.75 g) added and stirred at room temperature for 16 hours. The resin was removed by filtration and the filtrate washed with water (50 ml). The aqueous phase was purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to give 4-methyl-3-[4-oxo-6-(2-piperidin-1-ylethoxy)quinazolin-3(4H)-yl]benzoic acid (0.14 g); NMR Spectrum: (DMSOd$_6$) 1.42 (m, 6H), 2.13 (s, 3H), 2.48 (m, 4H), 2.72 (m, 2H), 4.20 (m, 2H), 7.49 (m, 2H), 7.56 (m, 1H), 7.69 (d, 1H), 7.88 (s, 1H), 7.96 (d, 1H), 8.15 (s, 1H); Mass Spectrum: M+H$^+$ 408.

EXAMPLE 7

3-[8-cyano-6-(4-methylpiperazin-1-yl)-4-oxo-quinazolin-3(4H)-yl]-N-isoxazol-3-yl-4-methylbenzamide Using an analogous procedure to that described paragraph (A) in the portion of Example 4, 3-[8-cyano-6-(4-methylpiperazin-1-yl)-4-oxoquinazolin-3(4H)-yl]-4-methylbenzoic acid was reacted with 3-aminoisoxazole to give 3-[8-cyano-6-(4-methylpiperazin-1-yl)-4-oxoquinazolin-3(4H)-yl]-N-isoxazol-3-yl-4-methylbenzamide; NMR Spectrum: (DMSOd$_6$) 2.19 (s, 3H), 2.24 (s, 3H), 2.49 (m, 4H), 3.35 (m, 4H), 7.04 (d, 1H), 7.61 (d, 1H), 7.70 (d, 1H), 8.11 (m, 3H), 8.30 (s, 1H), 8.84 (d, 1H), 11.46 (s, 1H); Mass Spectrum: M+H$^+$ 470.

3-[8-Cyano-6-(4-methylpiperazin-1-yl)-4-oxoquinazolin-3(4H)-yl]-4-methylbenzoic acid used for the starting material was prepared as follows:—

A solution of iodine monochloride (0.9 g) in glacial AcOH (1.7 ml) was added dropwise over 15 minutes to a stirred solution of 2-aminoisophthalic acid (1 g) in glacial AcOH (6.9 ml) at room temperature. The mixture was stirred for 2 hours and then poured into water (70 ml). The resultant orange solid was isolated by filtration, washed with water, diluted with MeOH and concentrated to yield 2-amino-5-iodoisophthalic acid (1.48 g); Mass Spectrum: M+H$^+$ 308.

To a suspension 2-amino-5-iodoisophthalic acid (30.4 g) and in toluene (300 ml) was added trimethyl orthoformate (60 ml) followed by acetic acid (5.6 ml). The reaction mixture was stirred at 100° C. for 4 hours when additional trimethyl orthoformate (30 ml) and acetic acid (5.6 ml) was added and the heating continued for a further 21 hours. Methyl 3-amino-4-methylbenzoate (10.9 g) was added and the reaction mixture stirred at 100° C. for 21 hours. The reaction mixture was cooled to room temperature and the resultant solid collected by filtration, washed MeOH and dried in vacuo for 18 hours to yield 6-iodo-3-[5-(methoxycarbonyl)-2-methylphenyl]-4-oxo-3,4-dihydroquinazoline-8-carboxylic acid as a white solid (21.1 g); NMR Spectrum: (DMSOd$_6$) 2.20 (s, 3H), 3.85 (s, 3H), 7.61 (d, 1H), 8.02 (m, 1H), 8.08 (s, 1H), 8.54 (m, 1H), 8.62 (m, 2H); Mass Spectrum: M+H$^+$ 465.

To a stirred solution of 6-iodo-3-[5-(methoxycarbonyl)-2-methylphenyl]-4-oxo-3,4-dihydroquinazoline-8-carboxylic acid (2.4 g) in 1,4-dioxane (50 ml) was added pyridine (0.42 ml), di-tert-butyl dicarbonate (1.47 g) and NH$_4$HCO$_3$ (0.53 g). The reaction mixture was stirred at 40° C. for 18 hours and concentrated. The resultant white solid was washed with methanol and dried to yield methyl 3-[8-(aminocarbonyl)-6-iodo-4-oxoquinazolin-3(4H)-yl]-4-methylbenzoate as a white solid (2.28 g); NMR Spectrum: (DMSOd$_6$) 2.19 (s, 3H), 3.85 (s, 3H), 7.61 (d, 1H), 8.03 (m, 3H), 8.52 (s, 1H), 8.60 (m, 1H), 8.70 (m, 1H), 9.33 (s, 1H); Mass Spectrum: M+H$^+$ 464.

To a stirred solution of methyl 3-[8-(aminocarbonyl)-6-iodo-4-oxoquinazolin-3(4H)-yl]-4-methylbenzoate in DMF (15 ml) was added thionyl chloride (1.79 ml). The reaction mixture was stirred at room temperature for 30 minutes and ice-water added. The resultant mixture was extracted with methylene chloride (×2) and the combined organic layers washed with water, saturated NaHCO$_3$ solution, dried (magnesium sulphate) and concentrated to yield methyl 3-(8-cyano-6-iodo-4-oxoquinazolin-3(4H)-yl)-4-methylbenzoate as a white solid (2.04 g); NMR Spectrum: (DMSOd$_6$) 2.19 (s, 3H), 3.88 (s, 3H), 7.61 (d, 1H), 8.03 (m, 2H), 8.53 (s, 1H), 8.67 (d, 1H), 8.74 (d, 1H); Mass Spectrum: M+H$^+$ 446.

Using an analogous procedure to that described paragraph (B) in the portion of Example 1 which is concerned with the preparation of starting material N-methyl piperazine was reacted with methyl 3-(8-cyano-6-iodo-4-oxoquinazolin-3(4H)-yl)-4-methylbenzoate to give methyl 3-[8-cyano-6-(4-methylpiperazin-1-yl)-4-oxoquinazolin-3(4H)-yl]-4-methylbenzoate; NMR Spectrum: (DMSOd$_6$) 2.19 (s, 3H), 2.24 (s, 3H), 2.49 (m, 4H, masked by DMSO), 3.36 (m, 4H), 3.88 (s, 3H), 7.63 (d, 1H), 7.70 (d, 1H), 8.03 (m, 2H), 8.13 (d, 1H), 8.28 (s, 1H); Mass Spectrum: M+H$^+$ 418.

Using an analogous procedure to that described paragraph (C) in the portion of Example 1 which is concerned with the preparation of starting material methyl 3-[8-cyano-6-(4-methylpiperazin-1-yl)-4-oxoquinazolin-3(4H)-yl]-4-methylbenzoate was hydrolysed with 1N NaOH to give 3-[8-cyano-6-(4-methylpiperazin-1-yl)-4-oxoquinazolin-3(4H)-yl]-4-methylbenzoic acid; Mass Spectrum: M+H$^+$ 404.

EXAMPLE 8

3-[8-Cyano-6-(4-ethylpiperazin-1-yl)-4-oxoquinazolin-3(4H)-yl]-N-isoxazol-3-yl-4-methylbenzamide Using an analogous procedure to that described paragraph (A) in the portion of Example 4, 3-[8-cyano-6-(4-ethylpiperazin-1-yl)-4-oxoquinazolin-3(4H)-yl]-4-methylbenzoic acid was reacted with 3-aminoisoxazole to give 3-[8-cyano-6-(4-ethylpiperazin-1-yl)-4-oxoquinazolin-3(4H)-yl]-N-isoxazol-3-yl-4-methylbenzamide; NMR Spectrum: (DMSOd$_6$) 1.03 (t, 3H), 2.19 (s, 3H), 2.38 (q, 2H), 2.53 (m, 4H), 3.35 (m, 4H), 7.04 (s, 1H), 7.60 (d, 1H), 7.69 (s, 1H), 8.10 (m, 3H), 8.29 (s, 1H), 8.84 (s, 1H), 11.47 (s, 1H); Mass Spectrum: M+H$^+$ 484.

3-[8-Cyano-6-(4-ethylpiperazin-1-yl)-4-oxoquinazolin-3(4H)-yl]-4-methylbenzoic acid used for the starting material was prepared as follows:—

Using an analogous procedure to that described paragraph (B) in the portion of Example 1 which is concerned with the preparation of starting material N-ethyl piperazine was reacted with methyl 3-(8-cyano-6-iodo-4-oxoquinazolin-3(4H)-yl)-4-methylbenzoate to give methyl 3-[8-cyano-6-(4-ethylpiperazin-1-yl)-4-oxoquinazolin-3(4H)-yl]-4-methylbenzoate; Mass Spectrum: M+H$^+$ 432.

Using an analogous procedure to that described paragraph (C) in the portion of Example 1 which is concerned with the preparation of starting material methyl 3-[8-cyano-6-(4-ethylpiperazin-1-yl)-4-oxoquinazolin-3(4H)-yl]-4-methylbenzoate was hydrolysed with 1N NaOH to give 3-[8-cyano-6-(4-ethylpiperazin-1-yl)-4-oxoquinazolin-3(4H)-yl]-4-methylbenzoic acid; Mass Spectrum: M+H$^+$ 418.

EXAMPLE 9

3-[6-[4-(cyclopropylmethyl)piperazin-1-yl]-4-oxoquinazolin-3(4H)-yl]-N-isoxazol-3-yl-4-methylbenzamide Using an analogous procedure to that described paragraph (A) in the portion of Example 4, 3-[6-[4-(cyclopropylmethyl)piperazin-1-yl]-4-oxoquinazolin-3(4H)-yl]-4-methylbenzoic acid was reacted with 3-aminoisoxazole to give 3-[6-[4-(cyclopropylmethyl)piperazin-1-yl]-4-oxoquinazolin-3(4H)-yl]-N-isoxazol-3-yl-4-methylbenzamide; NMR Spectrum: (DMSOd$_6$) 0.02 (m, 2H), 0.37 (m, 2H), 0.77 (m, 1H), 2.08 (s, 3H), 2.13 (m, 2H), 2.51 (m, 4H), 3.19 (m, 4H), 6.95 (s, 1H), 7.38 (s, 1H), 7.52 (m, 3H), 7.96 (m, 2H), 8.03 (s, 1H), 8.76 (s, 1H), 11.36 (s, 1H); Mass Spectrum: M+H$^+$ 485.

3-[6-[4-(cyclopropylmethyl)piperazin-1-yl]-4-oxoquinazolin-3(4H)-yl]-4-methylbenzoic acid used for the starting material was prepared as follows:—

Methyl 3-(6-bromo-4-oxoquinazolin-3(4H)-yl)-4-methylbenzoate (2 g), Cs$_2$CO$_3$ (4.4 g), racemic 2,2'-bis(diphenylphosphino)-1,1'-binaphthyl (0.67 g), palladium acetate (0.12 g) in anhydrous toluene (20 ml) at ambient temperature was added N-boc piperazine (2.5 g). The mixture was heated to 100° C. and stirred for 16 hours. Inorganic solids were removed via a hot filtration and the filtrate concentrated to give an oil. The oil was resuspended in MeOH (16 ml), 4N HCl in dioxane (10 ml) was added and the reaction mixture stirred at 50° C. for 1 hour when additional 4N HCl in dioxane (2 ml) was added and heating continued for a further 30 minutes. The reaction mixture was cooled to room temperature and the solid collected by filteration, washed with ethyl acetate (×2) and ether and dried. The resultant solid was suspended in saturated K$_2$CO$_3$ solution and extracted with ethyl acetate (×5). The organic layers combined, dried (magnesium sulphate) and concentrated to yield methyl 4-methyl-3-(4-oxo-6-piperazin-1-ylquinazolin-3(4H)-yl)benzoate as a yellow foam (1.41 g); NMR Spectrum: (DMSOd$_6$) 2.17 (s, 3H), 2.31 (m, 1H), 2.87 (m, 4H), 3.19 (m, 4H), 3.87 (s, 3H), 7.46 (s, 1H), 7.61 (m, 3H), 7.97 (s, 1H), 8.02 (d, 1H), 8.08 (s, 1H); Mass Spectrum: M+H$^+$ 379.

Methyl 4-methyl-3-(4-oxo-6-piperazin-1-ylquinazolin-3(4H)-yl)benzoate (1.41 g), (bromomethyl)cyclopropane (0.40 ml), and potassium carbonate (2.1 g) were stirred in DMF (9.4 ml) at 60° C. for 18 hours. The reaction mixture was diluted with ethyl acetate and washed with water (×3). The combined aqueous layers was extracted with EtOAc and the organic layers combined, washed with brine, dried (magnesium sulphate) and concentrated to yield a brown glass. MeOH was added and the resultant solid collected by filtration and washed with ethyl acetate to yield methyl 3-[6-[4-(cyclopropylmethyl)piperazin-1-yl]-4-oxoquinazolin-3(4H)-yl]-4-methylbenzoate as a white solid (0.39 g); NMR Spectrum: (DMSOd$_6$) 0.00 (m, 2H), 0.38 (m, 2H), 0.76 (m, 1H), 2.05 (s, 3H), 2.14 (d, 2H), 2.52 (m, 4H) 3.17 (m, 4H), 3.75 (s, 3H), 7.36 (s, 1H), 7.51 (m, 3H), 7.85 (s, 1H), 7.90 (d, 1H), 7.97 (s, 1H); Mass Spectrum: M+H$^+$ 433.

Using an analogous procedure to that described paragraph (C) in the portion of Example 1 which is concerned with the preparation of starting material methyl 3-[6-[4-(cyclopropylmethyl)piperazin-1-yl]-4-oxoquinazolin-3(4H)-yl]-4-methylbenzoate was hydrolysed with 1N NaOH to give 3-[6-[4-(cyclopropylmethyl)piperazin-1-yl]-4-oxoquinazolin-3(4H)-yl]-4-methylbenzoic acid; NMR Spectrum: (DMSOd$_6$) 0.42 (m, 2H), 0.68 (m, 2H), 1.15 (m, 1H), 2.16 (s, 3H), 3.07 (s, broad, 2H), 3.18 (s, 4H), 3.64 (s, broad, 2H), 4.02 (s, broad, 2H), 7.59 (m, 3H), 7.70 (m, 2H), 7.92 (s, 1H), 8.00 (d, 1H), 8.15 (s, 1H), 10.52 (s, broad, 1H), 13.06 (s, broad, 1H); Mass Spectrum: M+H$^+$ 419.

EXAMPLE 10

4-Methyl-N-(5-methylisoxazol-4-yl)-3-[6-(4-methylpiperazin-1-yl)-4-oxoquinazolin-3(4H)-yl]benzamide To a stirred slurry of 4-methyl-3-[6-(4-methylpiperazin-1-yl)-4-oxoquinazolin-3(4H)-yl]benzoic acid (0.38 g) in DMF (50 ml) was added 4-amino-5-methylisoxazole hydrochloride (0.27 g), HATU (0.68 g) and triethylamine (0.55 ml) and the reaction mixture stirred at room temperature for 16 hours. The reaction mixture was diluted with water and extracted with ethyl acetate. The ethyl acetate layer was washed with 1N NaOH and dried (magnesium sulphate). The residue was purified by column chromatography on a silica column using initially ethyl acetate and then a 4:1 mixture of ethyl acetate and methanol as eluent. There was thus obtained the title compound (150 mg); NMR Spectrum: (DMSOd$_6$) 2.15 (s, 3H), 2.40 (s, 3H), 2.83 (m, 4H), 3.15 (s, 3H), 3.40 (m, 4H), 7.50 (d, 1H), 7.60 (d, 1H), 7.64 (m, 2H), 7.98 (s, 1H), 8.04 (d, 1H), 8.13 (s, 1H), 8.70 (s, 1H), 10.10 (s, 1H); Mass Spectrum: M+H$^+$ 459.

The 4-amino-5-methylisoxazole hydrochloride used as starting material was prepared using the procedures detailed in J. Org. Chem. 1987, 2714-2716.

EXAMPLE 11

3-[6-{2-[Isopropyl(methyl)amino]ethoxy}-4-oxo-quinazolin-3(4H)-yl]-N-isoxazol-3-yl-4-methylbenzamide To a stirred slurry of 3-[6-{2-[isopropyl(methyl)amino]ethoxy}-4-oxoquinazolin-3(4H)-yl]-4-methylbenzoic acid (0.134 g) and DMF (0.05 ml) in methylene chloride (10 ml) at 50° C. was added thionyl chloride (0.15 ml). The resultant solution was stirred at 50° C. for 1 hour. The reaction mixture was concentrated and the resultant solid was redissolved in methylene chloride (10 ml), to this was added 3-aminoisoxazole (0.038 ml) and N,N-diisopropylethylamine (0.35 ml) and stirred for 3 hours. The solution was washed with water and concentrated. The mixture was purified by RP-HPLC (5-95% MeCN: 1% TFA in $H_2O$, 21 ml/min using a Waters Xterra Prep RP18 5 micron, 19×100 mm column). The fractions containing the product (as a TFA salt) where loaded directly onto an ion exchange column (isolute SCX column from International Sorbent Technology Limited, Henoed, Mid-Glamorgan, UK) washed initially methanol and the product eluted with a 99:1 mixture of methanol and aqueous ammonia solution to give 3-[6-{2-[Isopropyl(methyl)amino]ethoxy}-4-oxoquinazolin-3(4H)-yl]-N-isoxazol-3-yl-4-methylbenzamide (7 mg) Mass Spectrum: $M+H^+$ 462.

The 3-[6-{2-[isopropyl(methyl)amino]ethoxy}-4-oxo-quinazolin-3(4H)-yl]-4-methylbenzoic acid used for the starting material was prepared as follows:—

To a stirred solution of 3-[6-(2-chloroethoxy)-4-oxo-quinazolin-3(4H)-yl]-4-methylbenzoic acid (0.50 g), N-methylisopropylamine (0.58 ml), N,N-diisopropylethylamine (0.98 ml) and KI (0.47 g) in DMA (2 ml) was heated to 120° C. for 30 minutes in a microwave (Personal Chemistry Emrys Optimizer with 300 W magnetron). The reaction mixture was diluted with methylene chloride (20 ml), CombiZorb isocyanate resin (loading 1.03 mmol/g from Agilent) (6 g) added and stirred at room temperature for 16 hours. The resin was removed by filtration and the filtrate washed with water (50 ml). The aqueous phase was purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to give 3-[6-{2-[isopropyl(methyl)amino]ethoxy}-4-oxoquinazolin-3(4H)-yl]-4-methylbenzoic acid (0.135 g); Mass Spectrum: $M+H^+$ 396.

EXAMPLE 12

N-isoxazol-3-yl-4-methyl-3-[4-oxo-6-(2-pyrrolidin-1-ylethoxy)quinazolin-3(4H)-yl]benzamide To a stirred slurry of 4-methyl-3-[4-oxo-6-(2-pyrrolidin-1-ylethoxy)quinazolin-3(4H)-yl]benzoic acid (0.185 g) and DMF (0.05 ml) in methylene chloride (10 ml) at 50° C. was added thionyl chloride (0.21 ml). The resultant solution was stirred at 50° C. for 1 hour. The reaction mixture was concentrated and the resultant solid was redissolved in methylene chloride (10 ml), to this was added 3-aminoisoxazole (0.052 ml) and N,N-diisopropylethylamine (0.33 ml) and stirred for 3 hours. The aqueous phase was purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to give a black solid. The solid was triturated with ethyl acetate/iso-hexane, removed by filtration and the filtrate evaporated to give 3-[6-{2-[isopropyl(methyl)amino]ethoxy}-4-oxo-quinazolin-3(4H)-yl]-N-isoxazol-3-yl-4-methylbenzamide (22 mg); Mass Spectrum: $M+H^+$ 460.

The 4-methyl-3-[4-oxo-6-(2-pyrrolidin-1-ylethoxy)quinazolin-3(4H)-yl]benzoic acid used for the starting material was prepared as follows:—

To a stirred solution of 3-[6-(2-chloroethoxy)-4-oxo-quinazolin-3(4H)-yl]-4-methylbenzoic acid (0.50 g), pyrrolidine (0.46 ml), N,N-diisopropylethylamine (0.98 ml) and KI (0.47 g) in DMA (2 ml) was heated to 120° C. for 30 minutes in a microwave (Personal Chemistry Emrys Optimizer with 300 W magnetron). The reaction mixture was diluted with methylene chloride (20 ml), CombiZorb isocyanate resin (loading 1.03 mmol/g from Agilent) (6 g) added and stirred at room temperature for 16 hours. The resin was removed by filtration and the filtrate washed with water (50 ml). The aqueous phase was purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to give 4-methyl-3-[4-oxo-6-(2-pyrrolidin-1-ylethoxy)quinazolin-3(4H)-yl]benzoic acid (0.195 g); NMR Spectrum: ($DMSOd_6$) 1.70 (m, 4H), 2.13 (s, 3H), 2.64 (m, 4H), 2.92 (m, 2H), 4.24 (m, 2H), 7.53 (m, 3H), 7.69 (d, 1H), 7.89 (s, 1H), 7.96 (d, 1H), 8.15 (s, 1H); Mass Spectrum: $M+H^+$ 394.

EXAMPLE 13

N-isoxazol-3-yl-4-methyl-3-[6-[2-(1,4-oxazepan-4-yl)ethoxy]-4-oxoquinazolin-3(4H)-yl]benzamide To a stirred slurry of 4-methyl-3-[6-[2-(1,4-oxazepan-4-yl)ethoxy]-4-oxoquinazolin-3(4H)-yl]benzoic acid (0.29 g) and DMF (0.05 ml) in methylene chloride (10 ml) at 50° C. was added thionyl chloride (0.30 ml). The resultant solution was stirred at 50° C. for 1 hour. The reaction mixture was concentrated and the resultant solid was redissolved in methylene chloride (10 ml), to this was added 3-aminoisoxazole (0.076 ml) and N,N-diisopropylethylamine (0.48 ml) and stirred for 18 hours. The solution was washed with water and concentrated. The mixture was purified by RP-HPLC (5-95% MeCN: 1% TFA in $H_2O$, 21 ml/min using a Waters Xterra Prep RP18 5 micron, 19×100 mm column). The fractions containing the product (as a TFA salt) where loaded directly onto an ion exchange column (isolute SCX column from International Sorbent Technology Limited, Henoed, Mid-Glamorgan, UK) washed initially methanol and the product eluted with a 99:1 mixture of methanol and aqueous ammonia solution to give N-isoxazol-3-yl-4-methyl-3-[6-[2-(1,4-oxazepan-4-yl)ethoxy]-4-oxoquinazolin-3(4H)-yl]benzamide (19 mg); Mass Spectrum: $M+H^+$ 490.

The 4-methyl-3-[6-[2-(1,4-oxazepan-4-yl)ethoxy]-4-oxo-quinazolin-3(4H)-yl]benzoic acid used for the starting material was prepared as follows:—

To a stirred solution of 3-[6-(2-chloroethoxy)-4-oxo-quinazolin-3(4H)-yl]-4-methylbenzoic acid (0.50 g), 1,4-oxazepane hydrochloride (0.77 g), N,N-diisopropylethylamine (0.98 ml) and KI (0.47 g) in DMA (2 ml) was heated to 120° C. for 30 minutes in a microwave (Personal Chemistry Emrys Optimizer with 300 W magnetron). The reaction mixture was diluted with methylene chloride (20 ml), CombiZorb isocyanate resin (loading 1.03 mmol/g from Agilent) (6 g) added and stirred at room temperature for 16 hours. The resin was removed by filtration and the filtrate washed with water (50 ml). The aqueous phase was purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to give 4-methyl-3-[6-[2-(1,4-oxazepan-4-yl)ethoxy]-4-oxo-quinazolin-3(4H)-yl]benzoic acid (0.31 g); NMR Spectrum: (DMSOd$_6$) 1.87 (m, 2H), 2.10 (s, 3H), 2.91 (m, 2H), 3.02 (m, 4H), 3.66 (m, 4H), 4.20 (m, 2H), 7.46 (m, 2H), 7.58 (s, 1H), 7.69 (d, 1H), 7.81 (s, 1H), 7.93 (d, 1H), 8.16 (s, 1H); Mass Spectrum: M+H$^+$ 424.

EXAMPLE 14

3-[6-[4-(Cyclobutyl)piperazin-1-yl]-4-oxoquinazolin-3(4H)-yl]-N-isoxazol-3-yl-4-methylbenzamide Using an analogous procedure to that described paragraph (A) in the portion of Example 4, 3-[6-[4-(cyclobutyl)piperazin-1-yl]-4-oxoquinazolin-3(4H)-yl]-4-methylbenzoic acid was reacted with 3-aminoisoxazole to give 3-[6-[4-(cyclobutyl)piperazin-1-yl]-4-oxoquinazolin-3(4H)-yl]-N-isoxazol-3-yl-4-methylbenzamide; NMR Spectrum: (DMSOd$_6$) 1.74 (m, 2H), 1.96 (m, 2H), 2.07 (m, 2H), 2.28 (s, 3H), 2.55 (m, 4H), 2.83 (m, 1H), 3.39 (m, 4H), 7.20 (s, 1H), 7.46 (m, 1H), 7.53 (d, 1H), 7.67 (m, 2H), 7.85 (s, 1H), 7.91 (s, 1H), 7.99 (d, 1H), 8.26 (s, 1H); Mass Spectrum: M+H$^+$ 485.

3-[6-[4-(cyclobutyl)piperazin-1-yl]-4-oxoquinazolin-3(4H)-yl]-4-methylbenzoic acid used for the starting material was prepared as follows:—

To a solution of methyl 4-methyl-3-(4-oxo-6-piperazin-1-ylquinazolin-3(4H)-yl)benzoate (0.5 g) and cyclobutanone (0.20 ml) in THF (42.5 ml) was added titanium (IV) isopropoxide (0.75 ml) and the solution stirred at room temperature for 30 minutes. Sodium triacetoxyborohydride (0.83 g) was added and the reaction stirred at room temperature for 18 hours. Water was added and the resultant solid removed by filtration. The aqueous filtrate was washed with ethyl acetate. The organic layer was washed 1N NaOH (x2), water, brine, dried (magnesium sulphate) and to yield methyl 3-[6-[4-(cyclopropylmethyl)piperazin-1-yl]-4-oxoquinazolin-3(4H)-yl]-4-methylbenzoate as a yellow foam (0.45 g); NMR Spectrum: (DMSOd$_6$) 1.66 (m, 2H), 1.84 (m, 2H), 2.00 m, 2H), 2.16 (s, 3H), 2.42 (m, 4H), 2.75 (m, 1H), 3.27 (m, 4H), 3.87 (s, 3H), 7.48 (s, 1H), 7.62 (m, 3H), 7.97 (s, 1H), 8.02 (d, 1H), 8.09 (s, 1H); Mass Spectrum: M+H$^+$ 433.

Using an analogous procedure to that described paragraph (C) in the portion of Example 1 which is concerned with the preparation of starting material methyl 3-[6-[4-(cyclobutyl)piperazin-1-yl]-4-oxoquinazolin-3(4H)-yl]-4-methylbenzoate was hydrolysed with 1N NaOH to give 3-[6-[4-(cyclobutyl)piperazin-1-yl]-4-oxoquinazolin-3(4H)-yl]-4-methylbenzoic acid; NMR Spectrum: (DMSOd$_6$) 1.77 (m, 2H), 2.18 (s, 3H), 2.21 (m, 2H), 2.37 (m, 2H), 3.02 (m, 2H), 3.24 (m, 2H), 3.46 (m, 2H), 3.75 (m, 1H), 4.03 (m, 2H), 7.59 (m, 2H), 7.70 (m, 2H), 7.93 (s, 1H), 8.01 (d, 1H), 8.17 (s, 1H); Mass Spectrum: M+H$^+$ 419.

EXAMPLE 15

3-[6-{[(3S)-1-Isopropylpyrrolidin-3-yl]oxy}-4-oxo-quinazolin-3(4H)-yl]-N-isoxazol-3-yl-4-methylbenzamide To a stirred slurry of 3-[6-{[(3S)-1-isopropylpyrrolidin-3-yl]oxy}-4-oxoquinazolin-3(4H)-yl]-4-methylbenzoic acid (0.29 g) and DMF (0.05 ml) in methylene chloride (15 ml) at 0° C. was added thionyl chloride (0.15 ml). The resultant solution was stirred at room temperature for 21 hour. To this mixture was added 3-aminoisoxazole (0.316 ml) and the resultant solution was stirred for 18 hours. The reaction mixture was evaporated and the residue was dissolved in methanol and purified by column chromatography on an ion exchange column (isolute SCX column from International Sorbent Technology Limited, Henoed, Mid-Glamorgan, UK) using initially methanol and then a 99:1 mixture of methanol and aqueous ammonia solution. The fraction containing the product was further purified by column chromatography on an ion exchange column (isolute NH2 column from International Sorbent Technology Limited, Henoed, Mid-Glamorgan, UK) eluting with MeOH. After evaporation and the residue was dissolved in ethyl acetate and triturated with ether, the resultant solid was removed by filtration and isohexane was added to the filtrate and the resulting solid was filtered and dried to give 3-[6-{[(3S)-1-isopropylpyrrolidin-3-yl]oxy}-4-oxoquinazolin-3(4H)-yl]-N-isoxazol-3-yl-4-methylbenzamide as light tan solid (114 mg); NMR Spectrum: (DMSOd$_6$) 1.02 (m, 6H), 1.76 (m, 1H), 2.18 (s, 3H), 2.27 (m, 1H), 2.40 (m, 2H), 2.85 (m, 3H), 5.01 (m, 1H), 7.04 (m, 1H), 7.49 (m, 2H), 7.60 (d, 1H), 7.72 (d, 1H), 8.07 (m, 2H), 8.21 (s, 1H), 11.45 (s, 1H); Mass Spectrum: M+H$^+$ 474.

3-[6-{[(3S)-1-Isopropylpyrrolidin-3-yl]oxy}-4-oxo-quinazolin-3(4H)-yl]-4-methylbenzoic acid used for the starting material was prepared as follows:—

N-Cyclopropyl-4-methyl-3-[4-oxo-6-[(3S)-pyrrolidin-3-yloxy]quinazolin-3(4H)-yl]benzamide was synthesised using procedures detailed in WO2005/042502

A solution of N-Cyclopropyl-4-methyl-3-[4-oxo-6-[(3S)-pyrrolidin-3-yloxy]quinazolin-3(4H)-yl]benzamide (0.5 g) in 48% hydrobromic acid (5 ml) was heated to 130° C. for 30 minutes in a microwave (Personal Chemistry Emrys Optimizer with 300 W magnetron). The reaction mixture was diluted with ethyl acetate and extracted with water. The aqueous extracts were combined and purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to give 4-methyl-3-[4-oxo-6-[(3S)-pyrrolidin-3-yloxy] quinazolin-3(4H)-yl]benzoic acid as a solid (224 mg); NMR Spectrum: (DMSOd$_6$) 2.13 (m, 7H), 3.30 (m, 2H), 4.89 (s, 1H), 5.26 (s, 1H), 7.45 (m, 2H), 7.58 (t, 1H), 7.70 (d, 1H), 7.80 (s, 1H), 7.92 (m, 1H), 8.15 (s, 1H); Mass Spectrum: M+H$^+$ 366.

4-methyl-3-[4-oxo-6-[(3S)-pyrrolidin-3-yloxy]quinazolin-3(4H)-yl]benzoic acid (0.21 g) isopropyliodide (0.073 ml), and potassium carbonate (0.318 g) were stirred in dimethylacetamide (2 ml) for 18 hours at room temperature. Additional isopropyliodide (0.073 ml) was added and stirring continued for a further 24 hours. To the reaction mixture was added MeOH (2 ml), water (0.5 ml) and 2N NaOH (0.58 ml) and the reaction mixture was heated at 50° C. for 18 hours. The reaction mixture was purified by column chromatography on an ion exchange column (isolute SCX column from International Sorbent Technology Limited, Henoed, Mid- Glamorgan, UK) using initially methanol and then a 99:1 mixture of methanol and aqueous ammonia solution to give a brown oil which solidified on standing for 18 hours in vacuo to give 3-[6-{[(3S)-1-isopropylpyrrolidin-3-yl]oxy}-4-oxoquinazolin-3(4H)-yl]-4-methylbenzoic acid (297 mg); NMR Spectrum: (DMSOd$_6$) 0.99 (m, 6H), 1.80 (m, 1H), 2.13 (s, 3H), 2.33 (m, 2H), 2.78 (m, 4H), 5.03 (m, 1H), 7.46 (m, 3H), 7.70 (d, 1H), 7.87 (s, 1H), 7.96 (d, 1H), 8.16 (s, 1H); Mass Spectrum: M+H$^+$ 408.

EXAMPLE 16

N-isoxazol-3-yl-4-methyl-3-[6-(morpholin-4-ylmethyl)-4-oxoquinazolin-3(4H)-yl]benzamide Using an analogous procedure to that described paragraph (A) in the portion of Example 4, 4-methyl-3-[6-(morpholin-4-ylmethyl)-4-oxoquinazolin-3(4H)-yl]benzoic acid was reacted with 3-aminoisoxazole to give N-isoxazol-3-yl-4-methyl-3-[6-(morpholin-4-ylmethyl)-4-oxoquinazolin-3 (4H)-yl]benzamide; NMR Spectrum: (DMSOd$_6$) 2.21 (s, 3H), 2.41 (t, 4H), 3.60 (t, 4H), 3.65 (s, 2H), 7.06 (d, 1H), 7.62 (d, 1H), 7.77 (d, 1H), 7.87 (m, 1H), 8.10 (m, 2H), 8.15 (d, 1H), 8.32 (s, 1H), 8.86 (s, 1H), 11.47 (s, 1H); Mass Spectrum: M+H$^+$ 446.

3-[6-[4-(cyclopropylmethyl)piperazin-1-yl]-4-oxoquinazolin-3(4H)-yl]-4-methylbenzoic acid used for the starting material was prepared as follows:—

The 4-methyl-3-[6-(morpholin-4-ylmethyl)-4-oxoquinazolin-3(4H)-yl]benzoic acid used for the starting material was prepared as follows:—

To a solution of methyl 3-(6-bromo-4-oxoquinazolin-3 (4H)-yl)-4-methylbenzoate (5.00 g), bis(dibenzylideneacetone)palladium (0.19 g) and 1,2,3,4,5-pentaphenyl-1-(di-tert-butylphosphino)ferrocene (0.47 g) in anhydrous DMF (30 ml) under an argon atmosphere was added tert-butyl acrylate (4.3 ml) followed by triethylamine (4.5 ml). The reaction mixture was stirred at room temperature for 72 hours, then heated at 100° C. for 5 hours and poured onto brine. The resulting mixture was extracted with ethyl acetate and the combined organic layers were washed with water, dried (magnesium sulphate) and concentrated to give methyl 3-[6-[(1E)-3-tert-butoxy-3-oxoprop-1-en-1-yl]-4-oxoquinazolin-3(4H)-yl]-4-methylbenzoate as a solid (5.83 g). NMR Spectrum: (DMSOd$_6$) 1.51 (s, 9H), 2.20 (s, 3H), 3.88 (s, 3H), 6.67 (d, 1H), 7.63 (d, 1H), 7.75 (d, 1H), 7.77 (d, 1H), 8.04 (m, 2H), 8.28 (m, 1H), 8.34 (s, 1H), 8.40 (d, 1H); Mass Spectrum: M+H$^+$ 421.

To a mixture of methyl 3-[6-[(1E)-3-tert-butoxy-3-oxoprop-1-en-1-yl]-4-oxoquinazolin-3(4H)-yl]-4-methylbenzoate (1.11 g) and sodium periodate (1.24 g) in THF (20 ml) and water (6 ml) was added 2.5% wt solution of osmium tetroxide in tert-butanol (0.34 ml). The reaction was stirred at room temperature for 72 hours, diluted with THF (30 ml) and the precipitate removed by filtration. The resultant solution was concentrated and the residue dissolved in ethyl acetate, washed water/brine mixture, 10% aqueous solution of sodium thiosulfate (×2) and brine. The organic layers were concentrated to give a solid which was triturated with isohexane and collected by filtration to give methyl 3-(6-formyl-4-oxoquinazolin-3(4H)-yl)-4-methylbenzoate as a solid (0.54 g). NMR Spectrum: (DMSOd$_6$) 2.21 (s, 3H), 3.88 (s, 3H), 7.64 (d, 1H), 7.93 (d, 1H), 8.05 (m, 1H), 8.11 (d, 1H), 8.32 (m, 1H), 8.48 (s, 1H), 8.77 (d, 1H), 10.19 (s, 1H); Mass Spectrum: M+H$^+$ 323.

To a solution of methyl 3-(6-formyl-4-oxoquinazolin-3 (4H)-yl)-4-methylbenzoate (0.60 g) and titanium isopropoxide (1.10 ml) in methylene chloride (15 ml) was added morpholine (0.33 ml). The reaction was stirred at room temperature for 1 hour, then sodium triacetoxyborohydride (0.80 g) was added and stirred for a further 16 hours. The reaction mixture was diluted with water/methylene chloride (1:1) and filtered through diatomaceous earth (Celite®). The layers were separated, the aqueous layer extracted with methylene chloride. The combined organics were dried (magnesium sulphate) and concentrated to give a solid. The solid was purified by column chromatography on a silica column using initially methylene chloride and then a 19:1 mixture of methylene chloride and methanol as eluent to give methyl 4-methyl-3-[6-(morpholin-4-ylmethyl)-4-oxoquinazolin-3(4H)-yl]benzoate as a solid (0.62 g). NMR Spectrum: (DMSOd$_6$) 2.18 (s, 3H), 2.40 (m, 4H), 3.59 (m, 4H), 3.63 (s, 2H), 3.87 (s, 3H), 7.62 (d, 1H), 7.75 (d, 1H), 7.85 (m, 1H), 8.03 (m, 2H), 8.12 (d, 1H), 8.28 (s, 1H); Mass Spectrum: M+H$^+$ 394.

To a solution of methyl 4-methyl-3-[6-(morpholin-4-ylmethyl)-4-oxoquinazolin-3(4H)-yl]benzoate (0.62 g) in methanol (10 ml) and water (4 ml) was added 2N NaOH (2.35 ml) and stirred at room temperature for 4 hours. 1N HCl was added and the reaction was allowed to stand for 16 hours and then concentrated. The residue was dissolved in methanol (40 ml), inorganics removed by filtration. The filtrate concentrated to give 4-methyl-3-[6-(morpholin-4-ylmethyl)-4-oxoquinazolin-3(4H)-yl]benzoic acid as a solid (0.60 g). Mass Spectrum: M+H$^+$ 380.

EXAMPLE 17

3-[6-{2-[Dimethylamino]ethoxy}-4-oxoquinazolin-3 (4H)-yl]-N-isoxazol-3-yl-4-methylbenzamide Using an analogous procedure to that described paragraph (A) in the portion of Example 4, 3-[6-{2-[dimethylamino] ethoxy}-4-oxoquinazolin-3(4H)-yl]-4-methylbenzoic acid was reacted with 3-aminoisoxazole to give 3-[6-{2-[Dimethylamino]ethoxy}-4-oxoquinazolin-3(4H)-yl]-N-isoxazol-3-yl-4-methylbenzamide; NMR Spectrum: (DMSOd$_6$) 2.17 (s, 3H), 2.25 (s, 6H), 2.70 (m, 2H), 4.19 (m, 2H), 7.04 (s, 1H), 7.50 (d, 1H), 7.60 (m, 2H), 7.72 (m, 1H), 8.07 (m, 2H), 8.20 (m, 1H), 8.83 (s, 1H), 11.45 (s, 1H); Mass Spectrum: M+H$^+$ 434.

The 3-[6-{2-[dimethylamino]ethoxy}-4-oxoquinazolin-3 (4H)-yl]-4-methylbenzoic acid used for the starting material was prepared as follows:—

To a stirred solution of 3-[6-(2-chloroethoxy)-4-oxoquinazolin-3(4H)-yl]-4-methylbenzoic acid (0.27 g), dimethylamine hydrochloride (0.30 g), N,N-diisopropylethylamine (0.53 ml) and KI (0.25 g) in DMA (2 ml) was heated to 120° C. for 30 minutes in a microwave (Personal Chemistry Emmys Optimizer with 300 W magnetron). The reaction mixture was diluted with methylene chloride (20 ml), CombiZorb isocyanate resin (loading 1.03 mmol/g from Agilent) (6 g) added and stirred at room temperature for 16 hours. The resin was removed by filtration and the filtrate washed with water (50 ml). The aqueous phase was purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to give 3-[6-{2-[dimethylamino]ethoxy}-4-oxoquinazolin-3(4H)-yl]-4-methylbenzoic acid (0.10 g); NMR Spectrum: (DMSOd$_6$) 2.12 (s, 3H), 2.25 (s, 6H), 2.69 (m, 2H), 4.19 (m, 2H), 7.49 (m, 2H), 7.57 (s, 1H), 7.69 (d, 1H), 7.87 (s, 1H), 7.96 (d, 1H), 8.15 (s, 1H); Mass Spectrum: M+H$^+$ 368.

The invention claimed is:
1. A compound of Formula I

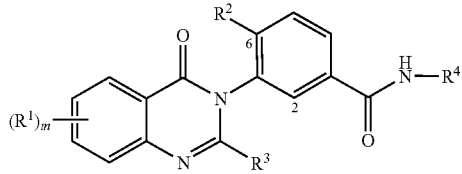

wherein
m is 0, 1 or 2;
R¹ is halogeno, hydroxy, cyano, trifluoromethyl, trifluoromethoxy, (1-6C)alkyl, (1-6C)alkoxy, (2-6C)alkenyl, (2-6C)alkynyl, (2-6C)alkanoyl, (1-6C)alkylthio, (1-6C)alkylsulphinyl, (1-6C)alkylsulphonyl, hydroxy-(2-6C)alkoxy, amino-(2-6C)alkoxy, cyano-(2-6C)alkoxy,(1-6C)alkylamino-(2-6C)alkoxy, di-[(1-6C)alkyl]amino-(2-6C)alkoxy, (1-6C)alkoxy-(2-6C)alkoxy, carbamoyl-(1-6C)alkoxy, N-(1-6C)alkylcarbamoyl-(1-6C)alkoxy, amino-(1-6C)alkyl, (1-6C)alkylamino-(1-6C)alkyl, di[(1-6C)alkyl]amino-(1-6C)alkyl, carbamoyl-(1-6C)alkyl, N-(1-6C)alkylcarbamoyl-(1-6C)alkyl, hydroxy-(2-6C)alkylamino, cyano-(2-6C)alkylamino, halogeno-(2-6C)alkylamino, amino-(2-6C)alkylamino, (1-6C)alkoxy-(2-6C)alkylamino, (1-6C)alkylamino-(2-6C)alkylamino, di-[(1-6C)alkyl]amino-(2-6C)alkylamino, heteroaryl, heteroaryl-(1-6C)alkyl, heteroaryloxy, heteroaryl-(1-6C)alkoxy, heteroarylamino, heterocyclyl, heterocyclyl-(1-6C)alkyl, heterocyclyloxy, heterocyclyl-(1-6C)alkoxy and heterocyclylamino,
wherein any aryl, heteroaryl or heterocyclyl group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl,
wherein any of the R¹ substituents defined hereinbefore which comprises a CH₂ group which is attached to 2 carbon atoms or a CH₃ group which is attached to a carbon or nitrogen atom may optionally bear on each said CH₂ or CH₃ group one or more substituents selected from halogeno, hydroxy, amino, trifluoromethyl, trifluoromethoxy, oxo, carboxy, carbamoyl, acetamido, (1-6C)alkyl, (2-6C)alkenyl, (2-6C)alkynyl, (3-6C)cycloalkyl, (3-6C)cycloalkoxy, (1-6C)alkoxy, (1-6C)alkylamino, di-[(1-6C)alkyl]amino, hydroxy-(1-6C)alkyl, (1-6C)alkoxy-(1-6C)alkyl, halogeno-(1-6C)alkyl, (1-6C)alkoxy-(2-6C)alkoxy, (1-6C)alkoxycarbonyl, carbamoyl, N-(1-6C)alkylcarbamoyl, N,N-di-[(1-6C)alkyl]carbamoyl, (1-6C)sulphonyl, (1-6C)sulphamoyl, heteroaryl, heteroaryl-(1-6C)alkyl, heterocyclyl and heterocyclyloxy,
wherein any heterocyclyl group in a R¹ substituent may optionally bear 1 or 2 oxo or thioxo substituents;
R² is halogeno, trifluoromethyl or (1-6C)alkyl;
R³ is hydrogen, halogeno or (1-6C)alkyl; and
R⁴ is isoxazolyl, and R⁴ may be optionally substituted by one or more substituents selected from halogeno, hydroxy, amino, (1-6C)alkyl, (2-6C)alkenyl, (2-6C)alkynyl, (1-6C)alkoxy, (1-6C)alkylamino and di-[(1-6C)alkyl]amino;
or a pharmaceutically-acceptable salt thereof.

2. The compound according to claim 1 wherein
R¹ is amino-(2-6C)alkoxy, (1-6C)alkylamino-(2-6C)alkoxy, di-[(1-6C)alkyl]amino-(2-6C)alkoxy, amino-(2-6C)alkylamino, (1-6C)alkylamino-(2-6C)alkylamino, di-[(1-6C)alkyl]amino-(2-6C)alkylamino, aryl, aryl-(1-6C)alkyl, aryl-(1-6C)alkoxy, aryloxy, arylamino, heteroaryl, heteroaryl-(1-6C)alkyl, heteroaryloxy, heteroaryl-(1-6C)alkoxy, heteroarylamino, heterocyclyl, heterocyclyl-(1-6C)alkyl, heterocyclyloxy, heterocyclyl-(1-6C)alkoxy or heterocyclylamino,
wherein any aryl, heteroaryl or heterocyclyl group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)-alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl,
wherein any of the R¹ substituents defined hereinbefore which comprises a CH₂ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino,
wherein any heterocyclyl group in a R¹ substituent may optionally bear 1 or 2 oxo or thioxo substituents;
or a pharmaceutically-acceptable salt thereof.

3. The compound according to claim 1 wherein
R¹ is heterocyclyl, heterocyclyl-(1-6C)alkyl, heterocyclyloxy, heterocyclyl-(1-6C)alkoxy or heterocyclylamino, and wherein any heterocyclyl group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl,
wherein any of the R¹ substituents defined hereinbefore which comprises a CH₂ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino;
or a pharmaceutically-acceptable salt thereof.

4. The compound according to claim 1 wherein $R^3$ is hydrogen or halogeno;
or a pharmaceutically-acceptable salt thereof.

5. The compound according to claim 1 wherein $R^2$ is (1-6C)alkyl;
or a pharmaceutically-acceptable salt thereof.

6. The compound according to claim 1 wherein $R^4$ is isoxazolyl, and $R^4$ may be optionally substituted by one or more substituents selected from halogeno and (1-6C)alkyl;
or a pharmaceutically-acceptable salt thereof.

7. The compound according to claim 1 wherein m is 1;
$R^1$ is heterocyclyl or heterocyclyloxy,
wherein any heterocyclyl group in a $R^1$ substituent may optionally bear 1 or 2 substituents selected from (1-6C)alkyl, (3-6C)cycloalkyl-(1-6C)alkyl, (1-6C)alkoxycarbonyl, (1-6C)alkoxycarbonyl-(1-6C)alkyl and hydroxy-(1-6C)alkyl;
$R^2$ is methyl;
$R^3$ hydrogen; and
$R^4$ is isoxazol-3-yl or isoxazol-5-yl;
or a pharmaceutically-acceptable salt thereof.

8. The compound according to claim 1 selected from:
N-isoxazol-3-yl-4-methyl-3-[6-(4-methylpiperazin-1-yl)-4-oxoquinazolin-3(4H)-yl]benzamide;
N-isoxazol-5-yl-4-methyl-3-[6-(4-methylpiperazin-1-yl)-4-oxoquinazolin-3(4H)-yl]benzamide;
3-[6-(4-isopropylpiperazin-1-yl)-4-oxoquinazolin-3(4H)-yl]-N-isoxazol-3-yl-4-methylbenzamide;
3-[6-(4-ethylpiperazin-1-yl)-4-oxoquinazolin-3(4H)-yl]-N-isoxazol-3-yl-4-methylbenzamide;
3-[6-(4-(2-methoxyethyl)piperazin-1-yl)-4-oxoquinazolin-3(4H)-yl]-N-isoxazol-3-yl-4-methylbenzamide;
N-isoxazol-3-yl-4-methyl-3-[4-oxo-6-(2-piperidin-1-ylethoxy)quinazolin-3(4H)-yl]benzamide;
3-[8-cyano-6-(4-methylpiperazin-1-yl)-4-oxoquinazolin-3(4H)-yl]-N-isoxazol-3-yl-4-methylbenzamide;
3-[8-Cyano-6-(4-ethylpiperazin-1-yl)-4-oxoquinazolin-3(4H)-yl]-N-isoxazol-3-yl-4-methylbenzamide;
3-[6-[4-(cyclopropylmethyl)piperazin-1-yl]-4-oxoquinazolin-3(4H)-yl]-N-isoxazol-3-yl-4-methylbenzamide;
4-Methyl-N-(5-methylisoxazol-4-yl)-3-[6-(4-methylpiperazin-1-yl)-4-oxoquinazolin-3 (4H)-yl]benzamide;
3-[6-{2-[Isopropyl(methyl)amino]ethoxy}-4-oxoquinazolin-3(4H)-yl]-N-isoxazol-3-yl-4-methylbenzamide;
N-isoxazol-3-yl-4-methyl-3-[4-oxo-6-(2-pyrrolidin-1-ylethoxy)quinazolin-3(4H)-yl]benzamide;
N-isoxazol-3-yl-4-methyl-3-[6-[2-(1,4-oxazepan-4-yl)ethoxy]-4-oxoquinazolin-3 (4H)-yl]benzamide;
3-[6-[4-(Cyclobutyl)piperazin-1-yl]-4-oxoquinazolin-3 (4H)-yl]-N-isoxazol-3-yl-4-methylbenzamide;
3-[6-{2-[Dimethylamino]ethoxy}-4-oxoquinazolin-3 (4H)-yl]-N-isoxazol-3-yl-4-methylbenzamide;
3-[6-{[(3S)-1-Isopropylpyrrolidin-3-yl]oxy}-4-oxoquinazolin-3(4H)-yl]-N-isoxazol-3-yl-4-methylbenzamide; and
N-isoxazol-3-yl-4-methyl-3-[6-(morpholin-4-ylmethyl)-4-oxoquinazolin-3(4H)-yl]benzamide;
or a pharmaceutically-acceptable salt thereof.

9. A pharmaceutical composition comprising the compound as claimed in claim 1, or a pharmaceutically-acceptable salt thereof, and a pharmaceutically-acceptable diluent or carrier.

* * * * *